United States Patent
Breunig et al.

(10) Patent No.: US 10,612,022 B2
(45) Date of Patent: Apr. 7, 2020

(54) ETS FACTORS REGULATE NEURAL STEM CELL DEPLETION AND GLIOGENESIS IN RAS PATHWAY GLIOMA

(71) Applicant: Cedars-Sinai Medical Center, Los Angeles, CA (US)

(72) Inventors: Joshua Breunig, Los Angeles, CA (US); Moise Danielpour, Los Angeles, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 0 days.

(21) Appl. No.: 15/575,721

(22) PCT Filed: May 20, 2016

(86) PCT No.: PCT/US2016/033630
§ 371 (c)(1),
(2) Date: Nov. 20, 2017

(87) PCT Pub. No.: WO2016/187586
PCT Pub. Date: Nov. 24, 2016

(65) Prior Publication Data
US 2018/0291375 A1 Oct. 11, 2018

Related U.S. Application Data

(60) Provisional application No. 62/164,475, filed on May 20, 2015.

(51) Int. Cl.
*G01N 33/50* (2006.01)
*A61K 38/17* (2006.01)
(Continued)

(52) U.S. Cl.
CPC ........ *C12N 15/113* (2013.01); *A61K 38/1709* (2013.01); *A61P 35/00* (2018.01);
(Continued)

(58) Field of Classification Search
CPC combination set(s) only.
See application file for complete search history.

(56) References Cited

U.S. PATENT DOCUMENTS 8,853,274 B1  10/2014  Wang

FOREIGN PATENT DOCUMENTS

WO    2016/187586 A1    11/2016

OTHER PUBLICATIONS

Breunig et al. Cell Reports. 2015 vol. 12:258-271.*
(Continued)

*Primary Examiner* — Terra C Gibbs
(74) *Attorney, Agent, or Firm* — Nixon Peabody LLP

(57) ABSTRACT

Described herein are composition and methods related to targeting the Nf1-Ras-Ets axis, that when perturbed, is identified as playing a role in initiation and maintenance in glioma. A postnatal, mosaic, autochthonous, glioma model that captures the first hours and days of gliomagenesis in more resolution than conventional genetically engineered mouse models of cancer demonstrates that disruption of the Nf1-Ras pathway in the ventricular zone at multiple signaling nodes uniformly results in rapid neural stem cell depletion, progenitor hyperproliferation, and gliogenic lineage restriction. By abolishing Ets subfamily activity, which is upregulated downstream of Ras, there is block of glioma initiation, thereby providing new therapeutic avenues for targeting glioma.

5 Claims, 16 Drawing Sheets
Specification includes a Sequence Listing.

(51) Int. Cl.
*C12N 15/113* (2010.01)
*A61P 35/00* (2006.01)

(52) U.S. Cl.
CPC ..... *G01N 33/5011* (2013.01); *G01N 33/5058* (2013.01); *C12N 2310/14* (2013.01); *C12N 2310/531* (2013.01)

(56) References Cited

OTHER PUBLICATIONS

International Search Report and Written Opinion for PCT/US2016/033630 dated Oct. 19, 2016, 10 pages.
Arcella et al., Rapamycin Inhibits the Growth of Glioblastoma, Brain Research, 2013, vol. 1495, pp. 37-51.
Banerjee et al., Neurofibromatosis-1 Regulates mTOR-Mediated Astrocyte Growth and Glioma Formation in a TSC/Rheb-Independent Manner, Proc. Nat. Acad. Sci., 2011, vol. 108(38), pp. 15966-16001.
Blum et al., Ras Inhibition in Glioblastoma Down-regulates Hypoxia-Inducible Factor-1α, Causing Glycolysis Shutdown and Cell Death, Cancer Res., 2005, vol. 65(3), pp. 999-1006.
Breunig et al., Ets Factors Regulate Neural Stem Cell Depletion and Gliogenesis in Ras Pathway Glioma, Cell Rep. ePub., 2015, vol. 12(2), pp. 258-271.
Wang et al., MiR-181d Acts as a Tumor Suppressor in Glioma by Targeting K-ras and Bcl-2., J. Cancer Res. Clin. Oncol, 2012, vol. 138, pp. 573-584.

* cited by examiner

A  Nf1 knockdown

B  Nf1 cKO

Nf1 floxed allele

+

Cre activity reporter
piggyBac FlEx-Transgene

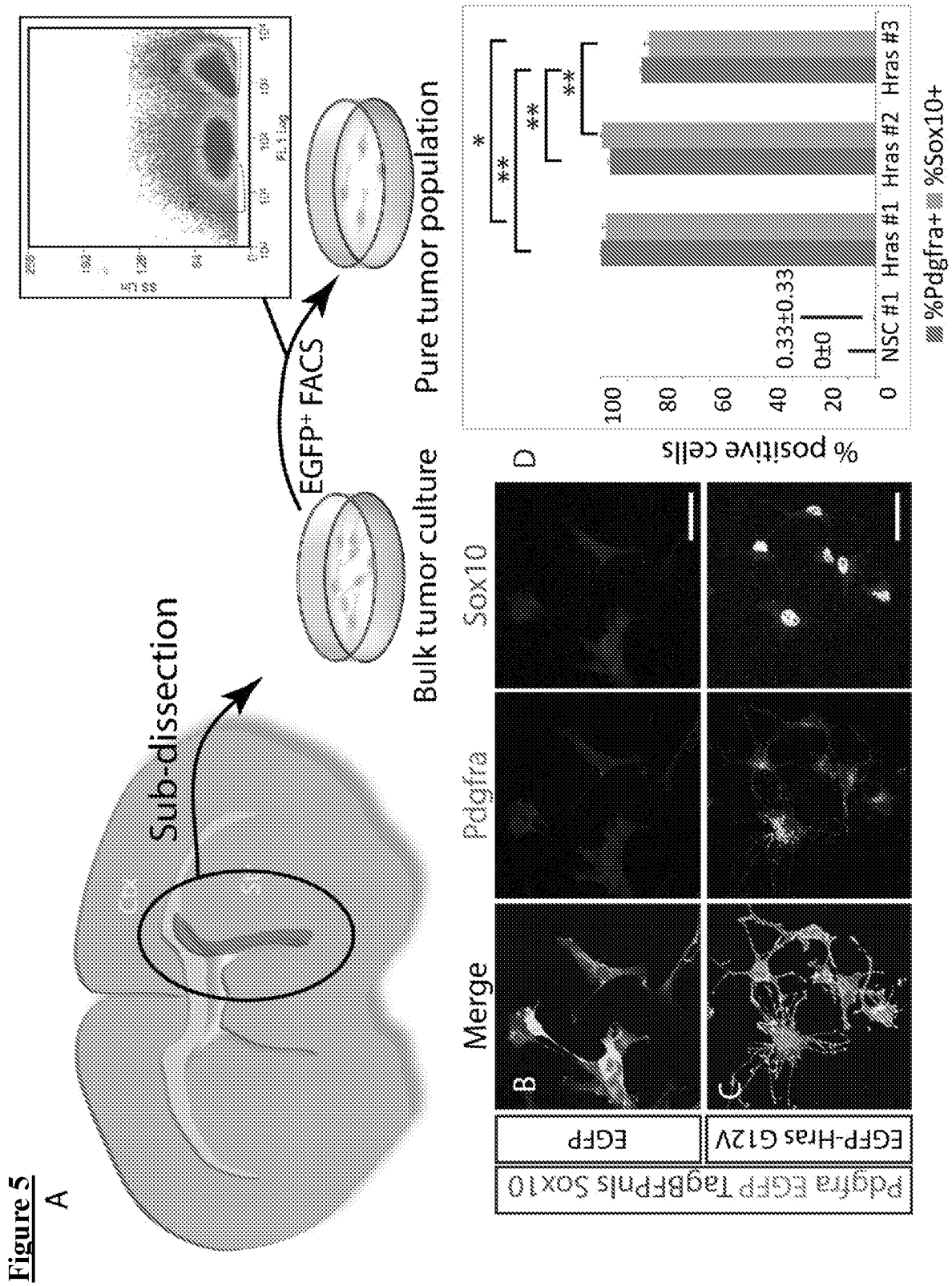

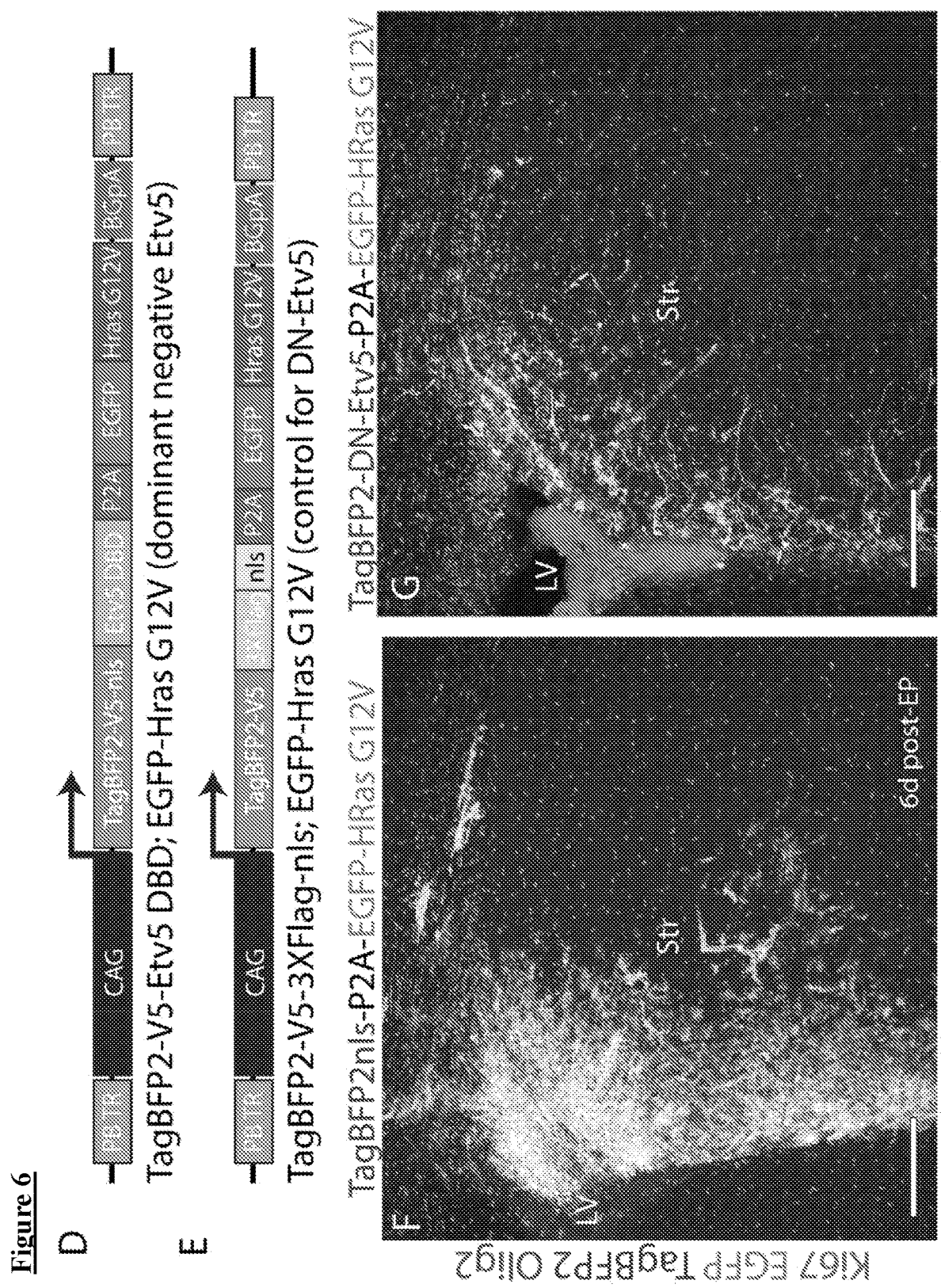

ETS FACTORS REGULATE NEURAL STEM CELL DEPLETION AND GLIOGENESIS IN RAS PATHWAY GLIOMA

CROSS-REFERENCE TO RELATED APPLICATIONS

This application is a National Phase of International Application No. PCT/US2016/03363 filed May 20, 2016, which designated the U.S. and that International Application was published under PCT Article 21(2) in English, which also includes a claim of priority under 35 U.S.C. § 119(e) to U.S. provisional patent application No. 62/164,475 filed May 20, 2015, the entirety of which is hereby incorporated by reference.

FIELD OF THE INVENTION

Described herein are methods and compositions for treating and managing cancer, including glioma, based on the discovery that ETS factors regulate neural stem cell depletion and gliogenesis.

BACKGROUND

High-grade gliomas are among the most fatal primary brain tumors and remain difficult to treat although recent advances in radiation and chemotherapy have added a few months of survival, albeit with side effects. Most treated primary gliomas inevitably evolve into secondary gliomas, which are almost always fatal. Understanding the molecular alteration(s) underlying the initial formation of tumors may determine critical steps required in the oncogenic process and may thereby lead to targeted therapies. Genetically engineered mouse models have been used to study initiating events in gliomagenesis by utilizing conditional knockout of tumor suppressors in promoter defined cell populations or by viral delivery of oncogenes. Commonly investigated themes include the cell(s) of mutation (i.e. cell in which the driver gene is mutated), the cell(s) of origin (the cancer initiating cell), and the nature of tumor propagating cells (proliferative cells contributing to tumor mass, which may not be able to generate the full repertoire of tumor cells) in glioma.

Initial findings suggested that brain tumor initiating cells display the properties of neural stem cells (NSCs), including the ability to self-renew and give rise to multiple daughter cell types. Additional studies provided evidence that oligodendrocyte progenitor cells (OPCs) can directly transform into symmetrically-expanding tumor-propagating cells upon acquisition of driver mutations. It remains unclear if these disparate findings reflect methodological differences or intrinsic differences in tumor types. Nevertheless, the resulting tumors in all of these models (and in patient tissue) are made up of cells histologically resembling glia, suggesting that signaling pathways necessary for gliogenesis might be required for glioma regardless of the cell of origin. Interestingly, the perinatal switch from neurogenesis to gliogenesis during development has recently been found to critically involve the Ras pathway—a pathway intimately linked to glioma. Direct Ras activating mutations (e.g. Ras G12V) display increased gliogenesis. Similarly, inactivating mutations to Nf1—a Ras inhibitor—and activating Pdgfra mutations are associated with glial proliferation and glioma. Moreover, conditional knockout of the downstream effectors of Ras, Mek1 and Mek2, led to abrogated developmental gliogenesis.

Described herein are methods and compositions related to the discovery that disrupting the Ras pathway in these cells drives a depletion of NSCs and an emergence of rapidly proliferating tumor cells that subsequently yield tumors with differing glioma subtype profiles and pathological grades. Ras-mediated glioblastic specification requires increased Ets activity and disrupting Ets signaling effectively reduces Ras-mediated NSC depletion and tumor formation. Therefore, the Ets family may represent a critical component in stem and progenitor cell genesis into glia and ultimately the formation of glioma.

SUMMARY OF THE INVENTION

Described herein is a method of treating glioma in a subject in need thereof including providing a quantity of a composition capable of modulating glioma initiation and/or maintenance and administering the quantity of the composition to the subject in need thereof, wherein modulation of glioma initiation and/or maintenance treats glioma in the subject. In various embodiments, the composition capable of modulating glioma initiation and/or maintenance modulates Nf1 and/or Ras. In various embodiments, the composition capable of modulating glioma initiation and/or maintenance modulates Ets. In various embodiments, the composition capable of modulating Ets comprises a small interfering RNA (siRNA) cognate to an Ets transcription factor. In various embodiments, the composition capable of modulating Ets comprises an agent capable of modifying post translational modification of Ets. In various embodiments, the post translational modification is provided by Rsk, Msk and/or P300. In various embodiments, the Ets is ETV5. In various embodiments, modulating Ets comprises an alteration in Ets binding to a target. In various embodiments, modulating Ets comprises an alteration in Ets expression level.

Also described herein is pharmaceutical composition comprising an agent capable of modulating Nf1, Ras, and/or Ets and a pharmaceutically acceptable carrier. In various embodiments, the agent comprises a small molecule. In various embodiments, agent comprises a peptide or protein. In various embodiments, agent comprises an antibody. In various embodiments, agent comprises a small interfering RNA (siRNA). In various embodiments, agent comprises an agent capable of modifying post translational modification of Ets. In various embodiments, post translational modification is provided by Rsk, Msk and/or P300. In various embodiments, Ets is ETV5. In various embodiments, modulating Ets comprises an alteration in Ets binding to a target. In various embodiments, modulating Ets comprises an alteration in Ets expression level.

BRIEF DESCRIPTION OF THE FIGURES

The patent or application file contains at least one drawing executed in color. Copies of this patent or patent application publication with color drawing(s) will be provided by the Office upon request and payment of the necessary fee.

(FIG. 1A) Postnatal electroporation of the VZ cells with EGFP-expressing plasmid. (FIG. 1B) pBase catalyzes the genomic integration of GOI. (FIG. 1C) Rate of stable expression by pBase-mediated integration, gene trapping, or episomal plasmid expression. Error bars±SEM; n=3. *$p<0.05$, **$p<0.01$, paired t-test (FIG. 1D-FIG. 1E) P2 coronal section taken 4 hrs after EP shows mostly RGs and few Ascl1+ and/or Olig2+ progenitors. (FIG. 1F-FIG. 1G$_4$, including FIG. 1G$_1$, FIG. 1G$_2$, FIG. 1G$_3$, FIG. 1G$_4$) P4 section EP-ed at P2 yields largely Vimentin+RGs and few non-VZ progenitors (arrowheads). The multipotent VZ cells EP-ed at P2 give rise to (FIG. 1H, FIG. 1J) neurons, (FIG. 1K) immature, and (FIG. 1L) mature oligodendrocytes, (FIG. 1M), astrocytes, and (FIG. 1N) multiciliated ependymal cells (FIG. 1I) 6-month section EP-ed at P2 confirms long-term stable expression. (Scale bars: A, D, F, H, I 100 μm; FIG. 1G and FIG. 1J-FIG. 1N, 10 μm.)

(FIG. 2A, FIG. 2B, FIG. 2C) Stitched images showing time-series development of Hras tumors. (FIG. 2D-FIG. 2E) MRI images of 3-week brains co-EP-ed with ferretin plus Hras or EGFP. (FIG. 2F, FIG. 2F$_2$) Micro-MRI showing ferritin+ tumor in the left hemisphere. (FIG. 2G) Survival analysis of control, Erbb2 CA, and Hras-G12V EP-ed mice. (FIG. 2H-FIG. 2I) Hras G12V animal present a domed skull and hydrocephalus in the left hemisphere (FIG. 2J) at moribundity. (FIG. 2K-FIG. 2P, including FIG. 2K, FIG. 2L, FIG. 2M, FIG. 2N, FIG. 2O, FIG. 2P) Pathological hallmarks of high-grade glioma at moribundity found in Hras tumor. (Magnification: FIG. 2K, FIG. 2M, FIG. 2N, FIG. 2O, 100×; FIG. 2L and FIG. 2P, 200×.)

(FIG. 3A-FIG. 3F, including FIG. 3A, FIG. 3B, FIG. 3C, FIG. 3D, FIG. 3E, FIG. 3F) P4 and P8 coronal sections of control, Erbb, and Hras brains stained with V5, EGFP, and Ki67. (F$_2$-F$_5$) Co-localization of Ki67, EGFP, and V5 in the boxed area from panel F. (FIG. 3G-FIG. 3H) Line chart comparing the quantification of EGFP-positive Ki67+ cells and the RGs at 2 d and 6 d after electroporations with control (FIG. 3A, FIG. 3D), Hras (FIG. 3C, FIG. 3F), Erbb (FIG. 3B, FIG. 3E), and WTHras (not shown). (FIG. 3I-FIG. 3N, including FIG. 3I, FIG. 3J, FIG. 3K, FIG. 3L, FIG. 3M, FIG. 3N) P4 and P8 coronal sections of control, Erbb, and Hras brains stained with V5, EGFP, Pdgfra, and Olig2. (FIG. 3M$_2$-FIG. 3M$_6$, including FIG. 3M$_2$, FIG. 3M$_3$, FIG. 3M$_4$, FIG. 3M$_5$, FIG. 3M$_6$) Co-localization of Pdgfra, EGFP, V5, and Olig2 in the boxed area from panel M (FIG. 3O) Line chart comparing the quantification of EGFP-positive Olig2+ at 2 d and 6 d after electroporations with control (FIG. 3I, FIG. 3L), Erbb (FIG. 3J, FIG. 3M), Hras (FIG. 3K, FIG. 3N), and WT-Hras (not shown). (FIG. 3P-FIG. 3U, including FIG. 3P, FIG. 3Q, FIG. 3R, FIG. 3S, FIG. 3T, FIG. 3U, FIG. 3V) P8 and P16 coronal sections of control, Erbb, and Hras brains stained with V5, EGFP, and Sox10. (FIG. 3U$_2$-FIG. 3U$_5$, including FIG. 3U$_2$, FIG. 3U$_3$, FIG. 3U$_4$, FIG. 3U$_5$) Co-localization of Sox10, EGFP, and V5 in the boxed area from panel U (FIG. 3V) Line chart comparing the quantification of EGFP-positive Sox10+ at 6 d and 2 wk after electroporations with control (FIG. 3P, FIG. 3S), Hras (FIG. 3R, FIG. 3U), Erbb (FIG. 3Q, FIG. 3T), and WT-HRas (not shown). Error bars±SEM; n=3 mice. *p<0.05, p<0.01, *p<0.001, ****p<0.0001, paired t-test. (Scale bar: A-F, I-N, P-U 25 μm)

(FIG. 4A) Schematic of Nf1 miR-E knockdown construct. (FIG. 4B) Strategy for floxed Nf1 mouse targeting by electroporation of Cre along with a FlEx Cre reporter. (FIG. 4C, FIG. 4D, FIG. 4E) WT CD1 brains EP-ed with shLuc, shNf1, and shNf1 plus NF1 cDNA. (FIG. 4F, FIG. 4G, FIG. 4H) Nf1fl/fl brains EP-ed with EGFP, Cre, and Cre plus NF1 cDNA. White arrows=RG fibers; Red arrowhead=truncated RG fiber; Orange arrowhead=glial clusters. Histograms showing the relative quantifications of the RGs by morphology in the brains shown by FIG. 4C-FIG. 4E. Histograms showing the relative quantifications of the RGs by morphology in the brains shown by FIG. 4C-FIG. 4H. Error bars±SEM; n=3 mice. *p<0.05, p<0.01, *p<0.001, paired t-test. (Scale bar: C-H 100 μm). FIG. 4I-FiG. 4J. % radial glia with shLuc, shNf1, and shNf1 plus NF1 and Nf1fl/fl blains EP-e with EGFP, Cre, and Cre plus NF1, respectively.

(FIG. 5A, FIG. 5B, FIG. 5C) Dissociated cells from the SVZ EP-ed with Hras but not control EGFP express Pdgfra and Sox10. Error bars±SEM. (Scale bar: FIG. 5B, FIG. 5C 25 μm). (FIG. 5D) Quantification of Sox10+ and Pdgfra+ cells in control NSC line and three different Hras G12V cell lines. (FIG. 5E) Transcriptome comparison of cultured tumor progenitors and NSC populations. (FIG. 5F) Classification of cell lines according to the four subtypes of human GBMs defined by TCGA with the single sample Gene Set Enrichment Analysis (ssGSEA) method.

(FIG. 6A) Increased Ets-family mRNA expression in tumor cells by microarray. (FIG. 6B) qRT-PCR confirmation of microarray data. (FIG. 6C, FIG. 6C$_2$) Nuclear Etv1 (aka Er81) expression in cortical EGFP+ tumor cells. (FIG. 6D-FIG. 6E) Plasmid schematics for bicistronic expression of DN-Etv5 and EGFP-Hras along with control containing TagBFP2-3× Flag-nls. Note that the P2A element ensures that all EGFP-Hras G12V cells will express upstream protein so that tumor cells can't "escape" DN-Etv5. (FIG. 6F-G) Coronal sections of Hras+3×Flag (FIG. 6F) and Hras+DN-Etv5 (FIG. 6G) brains at 6 d post-EP (Scale bars: A-C 50 μm.) (FIG. 6H, FIG. 6I, FIG. 6J) Comparison of Ki67+, Olig2, and RGs in Hras and Hras+DN-Etv5 brains. Error bars±SEM; n=3 mice. *p<0.05, **p<0.01, paired t test.

(FIG. 7A-FIG. 7B) Hemisphere images of Hras and Hras+DN-Etv5 brains. (FIG. 7A, FIG. 7B, FIG. 7C, FIG. 7D) 8-month long survival analysis indicates DN-Etv5 addition prevents morbidity (also compare with survival of animals in FIG. 2G.). (FIG. 7B) Eight months post-EP, DN-Etv5+EGFP-Hras G12V animals did not indicate any tumor presence. Cells did not express Sox10 or Olig2 (FIG. 7E, FIG. 7E$_1$, FIG. 7E$_2$; arrowheads denote EGFP-/Sox10+/Olig2+ cells), but did express the astrocytic markers AldoC and Aldh1l1 (FIG. 7F, FIG. 7F$_1$, FIG. 7F$_2$; red arrow denotes weakly Aldoc+/Aldh1l1+/EGFP+ cell whereas white arrows mark triple positive cells).

FIG. 8. Cell phenotyping criteria and expression of Erbb2 in ventricular zone radial glia. (FIG. 8A) Radial glia are identified based on morphological criteria, including VZ attachment of the cell body and a single basal process >100 μm. (FIG. 8B, FIG. 8B$_1$, FIG. 8B$_2$, FIG. 8B$_3$) Oligodendrocyte precursors and OPC-like tumor progenitors exhibited more sparse processes (white arrows in E1 showing inverted, grayscale fluorescent EGFP signal) and staining for Sox10 (FIG. 8B$_2$) and Olig2 (FIG. 8B$_3$) when compared with neighboring astrocytes (red arrowhead). (FIG. 8C, FIG. 8C$_1$, FIG. 8C$_2$, FIG. 8C$_3$) Morphologically, Astrocytes exhibited a dense cloud of processes, which was observed with EGFP (FIG. 8C, FIG. 8C$_1$), as well as Aldh1l1 (FIG. 8C$_2$), and Gfap (FIG. 8C$_3$) staining (see arrows).

FIG. 9. PiggyBac plasmid expression vectors, RTK/Kras tumorigenesis, examples from WT Hras and Errb2 overexpression, and pathological findings in Erbb2 V664E mice. (FIG. 9A) Expression vectors for the Clover-T2a-Erbb2 V664E, Erbb2 V664E, and Hras G12V-EGFP fusion protein. The Clover-T2a-V5-Erbb2 V664E self-cleavable protein and EGFP-Hras G12V fusion protein allow for unambiguous labeling of electroporated tumor cells by simultaneous EGFP labeling of cells. The V5 tag of the Erbb2 V664E transgene is located downstream of the signal peptide to ensure proper protein localization. (FIG. 9B) Mouse NSCs were nucleofected in vitro with control Clover-F, Clover-T2a-V5-Erbb2 V664E, and V5-Erbb2 V664E (all received TagBFP-3×flag-nls as a transfection control as well). Western blots display plasmid expression patterns, specifically showing the self-cleaving capabilities of the Clover-T2a-V5-Erbb2 V664E when blotted for EGFP. (FIG. 9C) Schematic of the control membrane-tagged EGFP plasmid in the PiggyBac vector, flanked with LTRs (PB TR) permitting stable integration into the genome when pBase is co-expressed. C-terminal Hras CAAX box is a farnesylation domain (Hras amino acids 170-189), inducing membrane localization. (FIG. 9D, FIG. 9E, FIG. 9F) Stitched images showing time-series development of Erbb tumors. (FIG. 9G-FIG. 9J, including FIG. 9G, FIG. 9H, FIG. 9I, FIG. 9J) Animals electroporated with Pdgfra D842V and Kras G12V show a similar radial glia depletion and tumorigenic phenotype at 6 days post-EP when compared with Erbb2 V664E and HRas G12V at the same time point. (FIG. 9G) Expression of Pdgfra D842V or (FIG. 9H) KRas-G12V shows evidence of NSC depletion and hyper-proliferation at six days. At three weeks both (FIG. 9I) Pdgfra D842V and (FIG. 9J) KRas G12V present as invasive tumors. (FIG. 9K) Expression of EGFP-Hras (wild type G12) or (FIG. 9L) wild type Erbb2 demonstrate radial glial maintenance at 6 days post-EP. (Compare with Erbb2 V664E [Main FIG. 3A] and HRas G12V [Main FIG. 3B] at the same time point. The identical expression vectors are employed with piggyBac integration.) (FIG. 9M, FIG. 9N, FIG. 9O) At moribundity, animals typically present tumor growths in the ventral forebrain (FIG. 9M-FIG. 9N), and (O) left hemisphere overgrowth due to electroporation in that ventricle. (FIG. 9P, FIG. 9Q, FIG. 9R) Pathological findings with Erbb2 V664E activating mutant were consistent with anaplastic high-grade glioma at moribundity, including palisading necrosis (FIG. 9P), infiltrating peripheral cell types (FIG. 9Q), and vascular proliferation (FIG. 9R). (Scale bar: FIG. 9G-FIG. 9H, FIG. 9K-FIG. 9L, 30 µm.)

FIG. 10. Counting frames, and effects of Ras mutations on human neural progenitor cell. (FIG. 10A) For each cell marker, all tissue at 2 and 6 days post-EP was counted using captured confocal zstack images along the SVZ lateral walls, as shown with an outlined box. 100 non-overlapping cells positive for TagBFP2 and EGFP were used to assess marker colocalization. (At 2 weeks, control EGFP electroporated tissue was quantified in the same manner as 2 and 6 day post electroporated tissue.) (FIG. 10B) 2 week Hras G12V and Erbb2-CA tissue was quantified. Fields along the outskirts and edges of the tumor were used to avoid counting within heavily dense tumor regions where necrosis often occurred. (However, counting in these regions resulted in highly similar results [CDA, JJB unpublished data]). (FIG. 10C, FIG. 10D, FIG. 10E, FIG. 10F) HuNPCs nucleofected with piggyBac-inserted membrane EGFP (i.e. EGFP-"Hras CAAX domain" fusion) and TagBFP2 (control) plasmids and cultured for 2 weeks exhibit GFAP expression and do not frequently immunostain with Olig2 antibody. (FIG. 10C$_1$, FIG. 10C$_2$) Red arrows indicating nuclear TagBFP2 and absence of Olig2 in these cells. Images of HuNPCs nucleofected with piggyBac-inserted EGFPHras-G12V (FIG. 10D, FIG. 10D$_1$, FIG. 10D$_2$) or EGFP-Kras G12V (FIG. 10E, FIG. 10E$_1$, FIG. 10E$_2$) and TagBFP2 plasmid and cultured for 2 weeks, demonstrating Olig2 expression and a lack of GFAP immunostaining (white arrows). (FIG. 10F) Hras/Kras-expression in HuNPCs results in robust increase in Olig2 expression and decrease in GFAP expression.

FIG. 11. Nf1 miR-E validation. (FIG. 11A) miR-E "sensor" plasmids designed to test 5 candidate Nf1 knockdown shRNA sequences. (FIG. 11B) Western blot revealed that all Nf1 miR-E's reduced EGFP expression from sensor better than previously characterized mir30 against EGFP. Nf1.789 was chosen due to potency, and the ability of this shRNA sequence (FIG. 11C) to "rescued" by codon-optimized human NF1 cDNA as shown by western blot (FIG. 11D). (FIG. 10E-FIG. 10F$_4$) Nf1.789-shRNA and Nf1.789-sensor were tested in vivo by EP alongside a previously characterized firefly luciferase-targeted (aka shLuc.1309) "control" shRNA. (FIG. 11E) Low magnification photomicrograph of distribution of TagRFP-t, EGFP (mirE Sensor NF1.789) and TagBFP2 immuno-stained cells. Arrowheads show diminished EGFP expression and an increased distribution of cells in the striatum. High magnification photomicrographs of show that the rare RG (square in E) shown in FIG. 11E1, FIG. 11E$_2$, FIG. 11E$_3$, FIG. 11E$_4$, exhibit EGFP and thus likely have residual Nf1 expression. (FIG. 11F-FIG. 11F$_4$, including FIG. 11F, FIG. 11F$_1$, FIG. 11F$_2$, FIG. 11F$_3$, FIG. 11F$_4$) EP of luciferase-targeting shRNA did not show diminished EGFP expression level of sensor NF1.789 when compared with cells in E-E$_4$. Cells were also found closer to the VZ (FIG. 11F) and many were RG (FIG. 11F$_3$). (FIG. 11G, FIG. 11G$_1$, FIG. 11G$_2$, FIG. 11G$_3$) human NF1 cDNA co-electroporated with Nf1.789 showed higher expression in RG (FIG. 11G$_1$). Note that the NF1cDNA appeared to rapidly dilute in progenitors (FIG. 11G$_1$) presumably due to its episomal behavior (i.e. not piggyBac inserted).

FIG. 12. Diminished neurogenic potential in Ras-expressing cells. (FIG. 12A) Two sequential electroporations (double EP) spaced at an 8-hr interval with two different plasmids targets distinct populations of cells undergoing desynchronized cell cycle. This example shows Cre recombinase in the first EP to inactivate floxedHras in the second EP, and subsequent dissociation of double EP brains to perform global single-cell lineage tracing. (FIG. 12B) Quantification of Olig2+, Dcx+, and GFAP+ cells in Cre/flox-Hras double EP brain dissociated and grown for 7 days in dish. Error bars±SEM; n=4 mice. (FIG. 12C-FIG. 12E) In vitro immunolabeling of the first EP (BglA; red) and second EP (Hras+TagBFP2; blue) cells with Olig2, Dcx, and Gfap (Scale bar: FIG. 12C, FIG. 12D, FIG. 12E, 50 µm). (FIG. 12F) Animals electroporated with control EGFP show normal neural stem cell differentiation into neural populations present in olfactory bulbs at two weeks post-EP. (FIG. 12G) EGFP-Hras G12V olfactory bulbs show markedly reduced numbers of neurons (FIG. 12G$_2$), a lack of cells exiting the rostral migratory stream at the core of the bulb, and dysmorphic cells in the granule cell layer (FIG. 12G$_1$). (Much of the signal in the granule cell layer (FIG. 12G$_3$) results from autofluorescent blood vessel signal.) (FIG. 12H) Erbb2-CA animals exhibit infiltration of the tumor into the olfactory bulbs at two weeks. (FIG. 12H$_1$) Few neurons are observed outside of the tumor. (Note, this is unstained, EGFP autofluorescence. Images were identically fixed, sectioned, and imaged. This was done to prevent artifactual normalization of EGFP intensity by antibody amplification. EGFP signal was converted to grayscale and inverted to increase contrast.)

FIG. 13. Analysis of tumor cell lines and transplantation. (FIG. 13A) Sequencing of cells from Erbb2, Hras and Kras tumor progenitors, demonstrates one or more secondary mutations were observed in the tumor suppressors, Trp53, p16, and p19. (FIG. 13B) Bilateral mouse brain 3 weeks post-transplant of 100,000 tumor cells, showing similar infiltrative and proliferative properties of tumors derived from electroporated Hras G12V cells. (FIG. 13C-FIG. 13D) Tumor progenitor cells express Sox10 and Olig2.

FIG. 14. Etv5 expression in the brain, plasmid validation, and DN-Etv5-expressing cell populations.

(FIG. 14A) Utilizing a newly-published dataset, RNA seq data displayed enriched expression of Ets family transcription factors in astrocytes and OPCs. (FIG. 14B) Plasmid schematics for expression of other variants of Etv5 in addition to those shown in FIG. 7D-E. (FIG. 14C) Proper nuclear localization of TagBFP2DN-Etv5 in the nucleus and membrane EGFP-Hras expressed from the P2A-based plasmid in FIG. 7D. (FIG. 14D) SRE-driven firefly luciferase demonstrates hyperactivity of Hras in P2A-based DN-Etv5 plasmid. (FIG. 14E) Pea3driven luciferase assay data shown to confirm activity of DN-Etv5 plasmids shown FIG. 7D-E and FIG. 14B.

FIG. 15. Schematic of overall study design.

FIG. 16. Pea3 responsive luciferase assay. Overexpression of unmodified Etv5 alone does not incite maximal transactivation of response promoters. (FIG. 16A) mimicking constitutively active Etv5 (Etv5-VP64) in reporter assay increases transcription factor activity (FIG. 16B) Supplementing wt Etv5 with PTM affecters Rsk1, Msk1, and P300 increase transactivation potential of wt Etv5. However, not as potent as Etv-VP64. (FIG. 16C) PKA robustly increases Pea3-luc activity. (FIG. 16D) P300 and PKA display synergistic effects on induction of Pea3-luc by Etv5.

FIG. 17. Ets-family transcription factors expression in glioma. (FIG. 17A) TCGA data indicate decreased survival in Etv5 amplified glioma patients. (FIG. 17B) qRT-PCR confirmation of Ets mRNA abundance in multiple models, including a "personalized" pediatric GBM combination with H3F3a, Trp53, and Pdgfra mutations.

Figure 1:
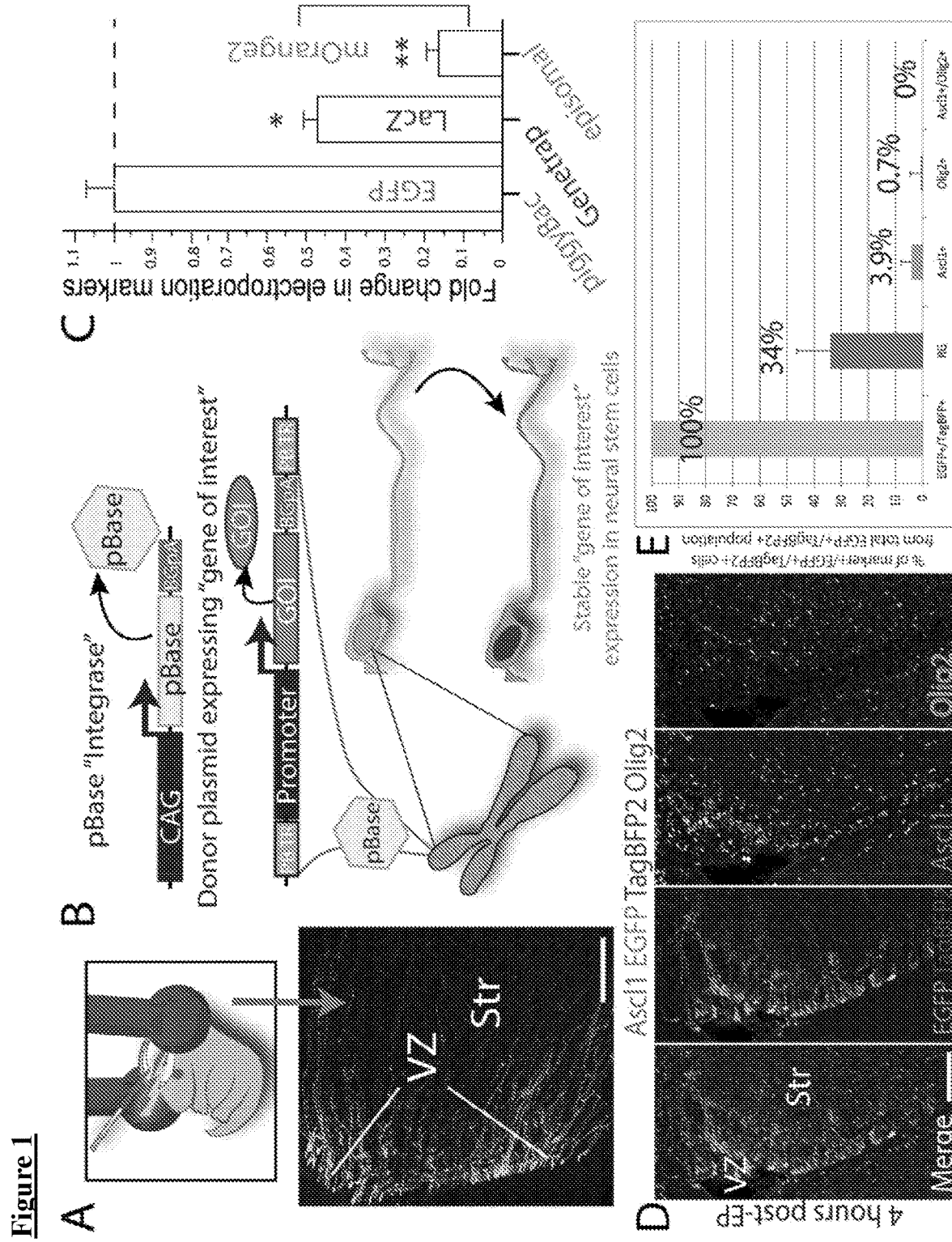
FIG. 1: Postnatal electroporation combined with piggyBac transposition targets NSCs and progenitor cells and provides sustained transgene expression.
Figure 1:
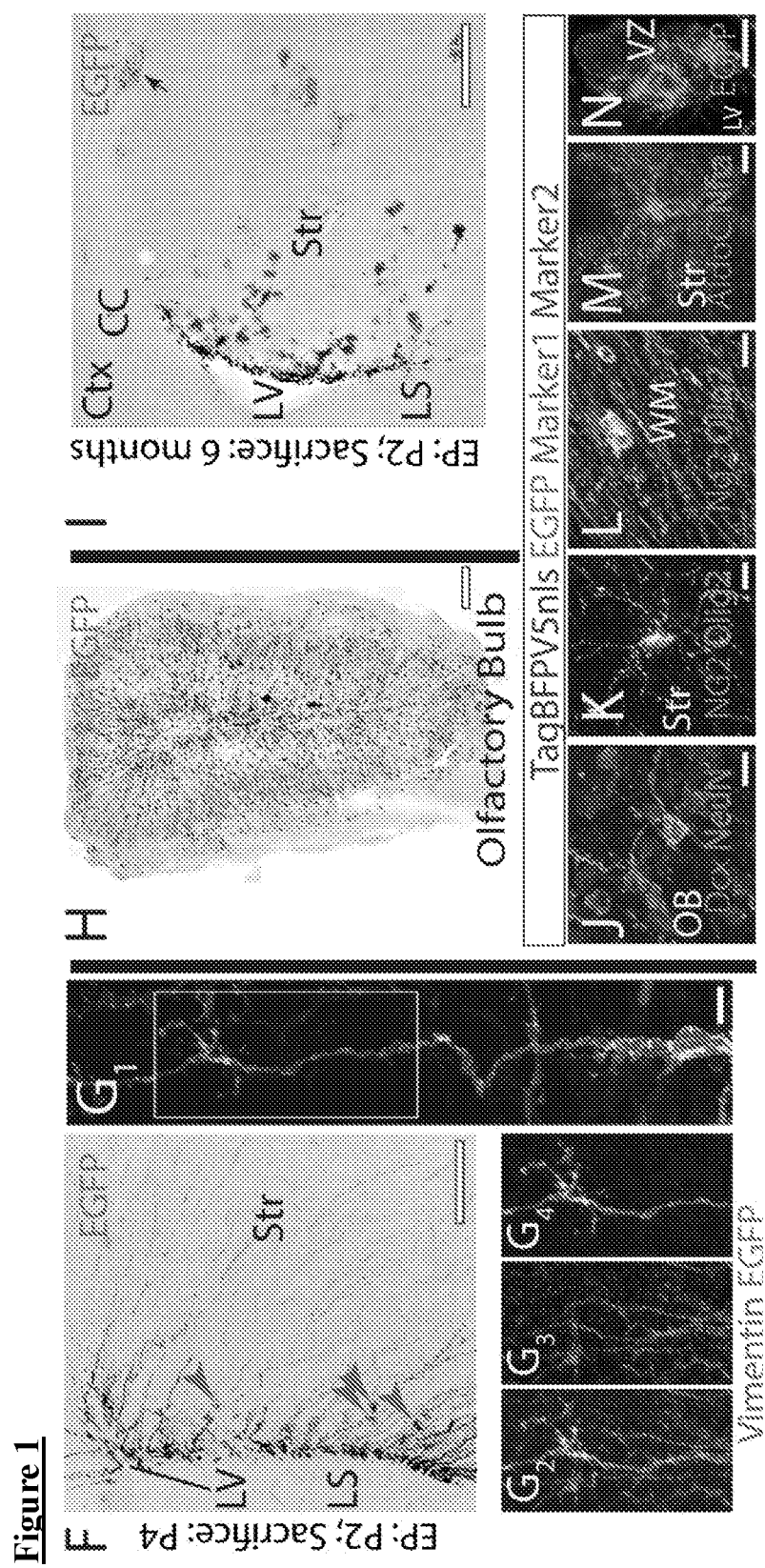

As the list of putative driver mutations in glioma grows, researchers are only beginning to elucidate the effects of dysregulated developmental signaling pathways on the transformation of neural cells. The Inventors have employed a postnatal, mosaic, autochthonous, glioma model that captures the first hours and days of gliomagenesis in greater resolution than conventional genetically engineered mouse models of cancer. This approach provides evidence that disruption of the Nf1-Ras pathway in the ventricular zone at multiple signaling nodes uniformly results in rapid neural stem cell depletion, progenitor hyperproliferation, and gliogenic lineage restriction. Abolishing Ets subfamily activity, which is upregulated downstream of Ras, rescues these phenotypes and blocks glioma initiation. Thus, the Nf1-Ras-Ets axis might be one of the select molecular pathways that are perturbed for initiation and maintenance in glioma. Described herein are results demonstrating Etv5, a member of the Ets transcription factor family, as a likely mediator of perinatal gliogenesis.

Towards investigating the specification of glial cells during glioma initiation, the Inventors focally targeted the postnatal day 2 ventricular zone (VZ) by combining electroporation (EP) with piggyBac transposition. This allows for mosaic genetic modification of the proliferating NSC and progenitor populations. Specifically, the Inventors hyperactivated the Ras pathway either by EP of Kras or Hras G12V mutants, or by EP of Pdgfra or Erbb2 receptor mutants. Additionally, Ras was disinhibited through Nf1 knockdown or knock out by directly targeting Nf1 with state-of-the-art miR-E based shRNAs or using Nf1 floxed mice.

The ability of this model to track the transformative events resulting from disparate mutations in NSCs and progenitors with fluorescent genetic reporters led to the discovery of common events occurring during tumorigenesis.

Described herein is a method of treating glioma in a subject in need thereof comprising providing a quantity of a composition capable of modulating a glioma initiation and/or maintenance, administering the quantity of the composition to the subject in need thereof, wherein modulation of glioma initiation and/or maintenance treats glioma in the subject. In various embodiments, the composition capable of modulating a glioma initiation and/or maintenance modulates the Nf1 and/or Ras. In various embodiments, the composition capable of modulating a glioma initiation and/or maintenance modulates Ets. Ets family members are identified through a highly conserved DNA binding domain, the Ets domain, a winged helix-turn-helix structure that binds to DNA sites with a central GGA(A/T) DNA sequence.

In various embodiments, the composition capable of Ets comprises a small interfering RNA (siRNA) cognate to an Ets transcription factor. In various embodiments, the composition capable of modulating Ets comprises an agent capable of modifying post translational modification of Ets. In various embodiments, post translational modification is provided by Rsk, Msk and/or P300. For example, 1,3,5-triazine small molecule BRD32048 is a ETV1 perturbagen, binding to ETV1 directly and p300-dependent acetylation. In this regard, a histone acetyltransfer (HAT) inhibitor may serve to modulate Ets activity. Another molecule, YK-4-279, which modulates several ETS family members including ERG, ETV1, and FLI1. In various embodiments, Ets is ETV5. In various embodiments, modulating Ets comprises an alteration in Ets binding to a target. In various embodiments, modulating Ets comprises an alteration in Ets expression level.

Also described herein is a pharmaceutical composition comprising an agent capable of modulating Nf1, Ras, and/or Ets and a pharmaceutically acceptable carrier. In various embodiments, the agent comprises a small molecule. In various embodiments, the agent comprises a peptide or protein. In various embodiments, the peptide or protein is a dominant negative Ets. In various embodiments, agent comprises an antibody. In various embodiments, agent comprises a small interfering RNA (siRNA). In various embodiments, the composition capable of modulating Ets comprises an agent capable of modifying post translational modification of Ets. In various embodiments, post translational modification is provided by Rsk, Msk and/or P300. In various embodiments, Ets is ETV5. In various embodiments, modulating Ets comprises an alteration in Ets binding to a target. In various embodiments, modulating Ets comprises an alteration in Ets expression level.

EXAMPLES

The following examples are provided to better illustrate the claimed invention and are not to be interpreted as limiting the scope of the subject matter. To the extent that specific materials are mentioned, it is merely for purposes of illustration and is not intended to limit the invention. One skilled in the art may develop equivalent means, compositions or reactants without the exercise of inventive capacity and without departing from the scope of the present invention.

Example 1

Mice and Electroporation

CD1 mice were used for all experiments, which were performed according to the Cedars-Sinai Institutional Animal Care and Use Committee. Postnatal lateral ventricle electroporations were performed as previously described. Briefly, postnatal day 1-2 pups were placed on ice for ~8 minutes until unresponsive to tail pressure. 1.2 μl of a plasmid DNA mix (typically 1.0 μg/μl) in Tris-EDTA buffer was injected into the left lateral ventricle. Plasmid details are available in Table 1. Employing Signagel, platinum Tweezertrodes were used to EP with three to five pulses of 115-135 V (50 ms; separated by 950 ms) generated using the ECM 830 BTX Electroporator (Harvard Apparatus).

Example 2

Tissue Preparation

After anesthesia, mouse brains were isolated and immersion fixed in 4% ice-cold paraformaldehyde (PFA) overnight. Brains were then embedded in low melting point 4% agarose and sectioned at 70 μm on a vibratome. For Errb2 immunohistochemistry, mice were transcardially perfused.

Example 3

Imaging

All confocal images were collected on a Nikon A1R or C2 inverted laser confocal microscope. For hemi or whole brain images, the automated stitching function of Nikon Elements was used to create a seamless merged image from multiple image fields.

Example 4

Purification of EGFP+ Tumor Cells

EGFP+"WT" NSCs and EGFP+ tumor cells from a tumor-bearing animal were first microdissected from the left hemisphere, digested in accutase, and grown as monolayers according to the Inventors' previously-described methods. After growing to confluence, cells underwent FACS for EGFP autofluorescence and were cultured as self-renewing monolayers.

Example 5

RNA Isolation, Microarray, and Gene Expression Analysis

RNA from EGFP+ NSCs and EGFP+ tumor cells was isolated using RNeasy+ Kits according to manufacturer's protocols and hybridized to Affymetrix Mouse Genome ST microarrays. Analysis of differential gene expression was performed using dChip. Neural cell type classification and ssGSEA were performed as previously.

Example 6

Tissue Processing

After harvesting, mouse brains were fixed in a 4% paraformaldehyde (in phosphate-buffered saline, PBS) mixture for 12 to 15 hours at 4° C. The brains were then embedded in 4% low-melt agarose (in PBS). Brains were cut coronally into 70 um sections using a Vibratome.

Example 7

Tissue Immunostaining

A primary antibodies mixture was made in PBS-Triton (PBS-T, 0.3% triton) with at least 3.0% normal donkey serum (NDS) and the desired primary antibodies at the ratios indicated in Table 2. The tissue sections were incubated with the primary antibody mixture for at least 12 hours at 4° C. The tissue was then washed three times for 5 min with PBS at room temperature. Secondary antibody mixtures were made with PBS-T and the appropriate secondary antibodies at a 1:1000 dilution (Jackson Immunoresearch; conjugated with Alexa 405, Fitc, Alexa488, Dylight488, Alexa555, Dylight549, Alexa647, or Dylight649). This mixture was added to the sections and which were incubated shaking at room temperature for 1 hour. The Inventors' tumor genes were frequently conjugated to EGFP, RFP, or TagBFP2, and in these cases the Inventors used primary antibodies specific for those tags (e.g. V5 in the case of TagBFP2-V5-nls) and secondary antibodies in the same color channel. The sections were washed in PBS, mounted on slides and allowed to dry for at least 3 hours. The dry tissue was coated with an anti-fade mounting gel medium (Invitrogen ProLong) and coverslips were placed.

Example 8

Olfactory Bulb Imaging

Unstained olfactory bulbs were mounted on glass slides and coverslipped. Stitched images were collected in an automated fashion using Nikon elements. Immunohistochemical amplification of EGFP signals was omitted preclude the artifactual, non-linear normalization of signal intensity observed following EGFP antibody staining.

Example 9

Image Processing

ND2 image files were initially imported into ImageJ for creating projections from confocal zstacks or for isolation of individual channels from single zslices for pasting into Adobe Photoshop CS6. Image curves were adjusted for consistence of dynamic range in Photoshop CS6, cropped, and then pasted into Adobe Illustrator CS6 for the preparation of final images. In some cases, color channels were converted to grayscale and inverted to reveal fine details (e.g. EGFP). As mentioned, image stitching of whole/hemi brain images was accomplished in an automated fashion using the tiling function in Nikon Elements. In the case of projected zstack images, stacks were collected using identical settings and every attempt was made to display comparable final projections (i.e. similar numbers of projected zstack images.)

Example 10

Quantification of Markers

Animals were electroporated with a BFP2 nuclear protein and either a EGFP membrane protein and Erbb2 CA or HRas G12V fused EGFP protein.

For each group, animals were euthanized and tissue was collected at 2 day, 6 day and 2 weeks post electroporation (N=3 brains for each age group). Fixed brains were coronally sectioned into 70 um sections. Two to four sections containing the septal VZ/SVZ region were stained and processed for data collection.

For each group the stained sections were imaged along the VZ/SVZ region with at least two images per animal. For each animal 100 nuclear TagBFP2 positive cells were counted. These cells were then quantified as positive or negative for EGFP. The cells positive for both BFP and EGFP were further quantified as positive or negative for the specific cell markers (Ki67, Olig2, PDGFRα, or Sox10). In all time points prior to obvious hyperproliferation, cells were counted within a 10 cell diameter thickness from the ventricle. In time points with hyperproliferation, cells were counted within the VZ/SVZ in regions where single cells could be deciphered.

Example 11

Quantification of Radial Glia

Figure 4:
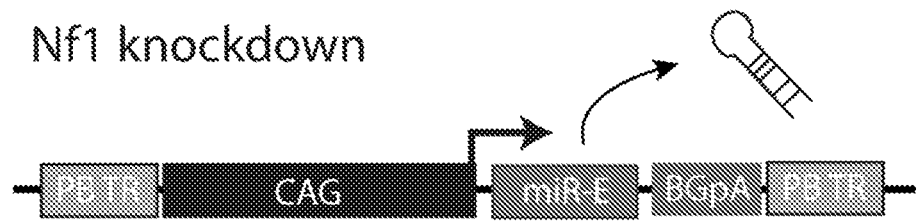
FIG. 4: Nf1 loss of function through knockdown or conditional knockout shows significant reduction in radial glia and striatal gliogenesis.
Figure 4:
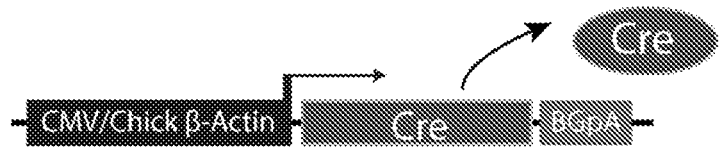
Figure 4:
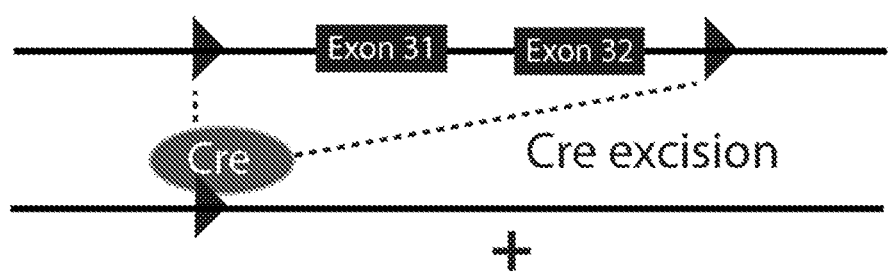
Figure 4:
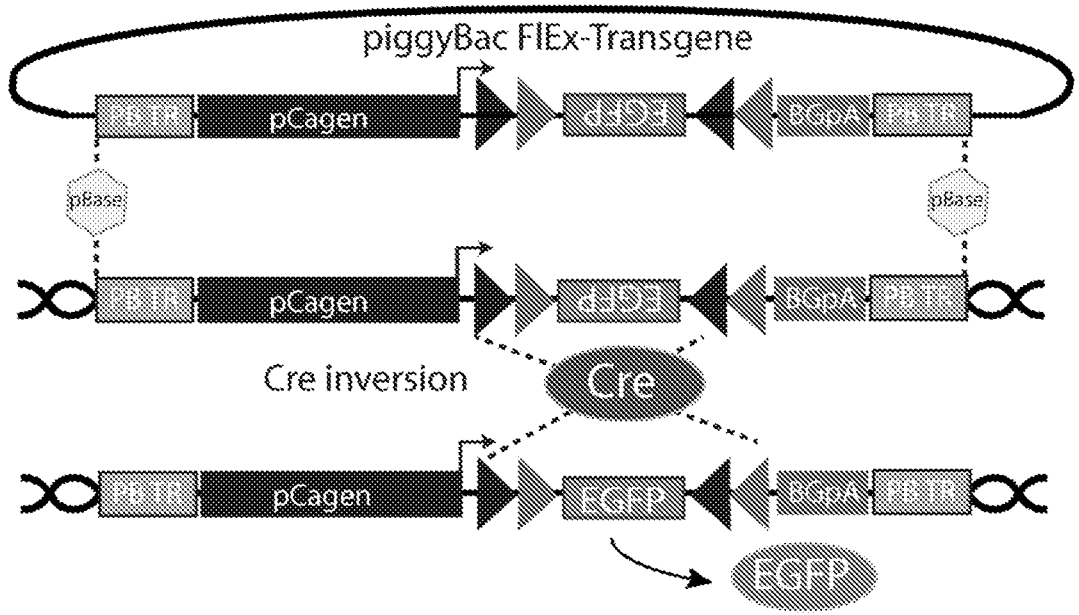
Figure 4:
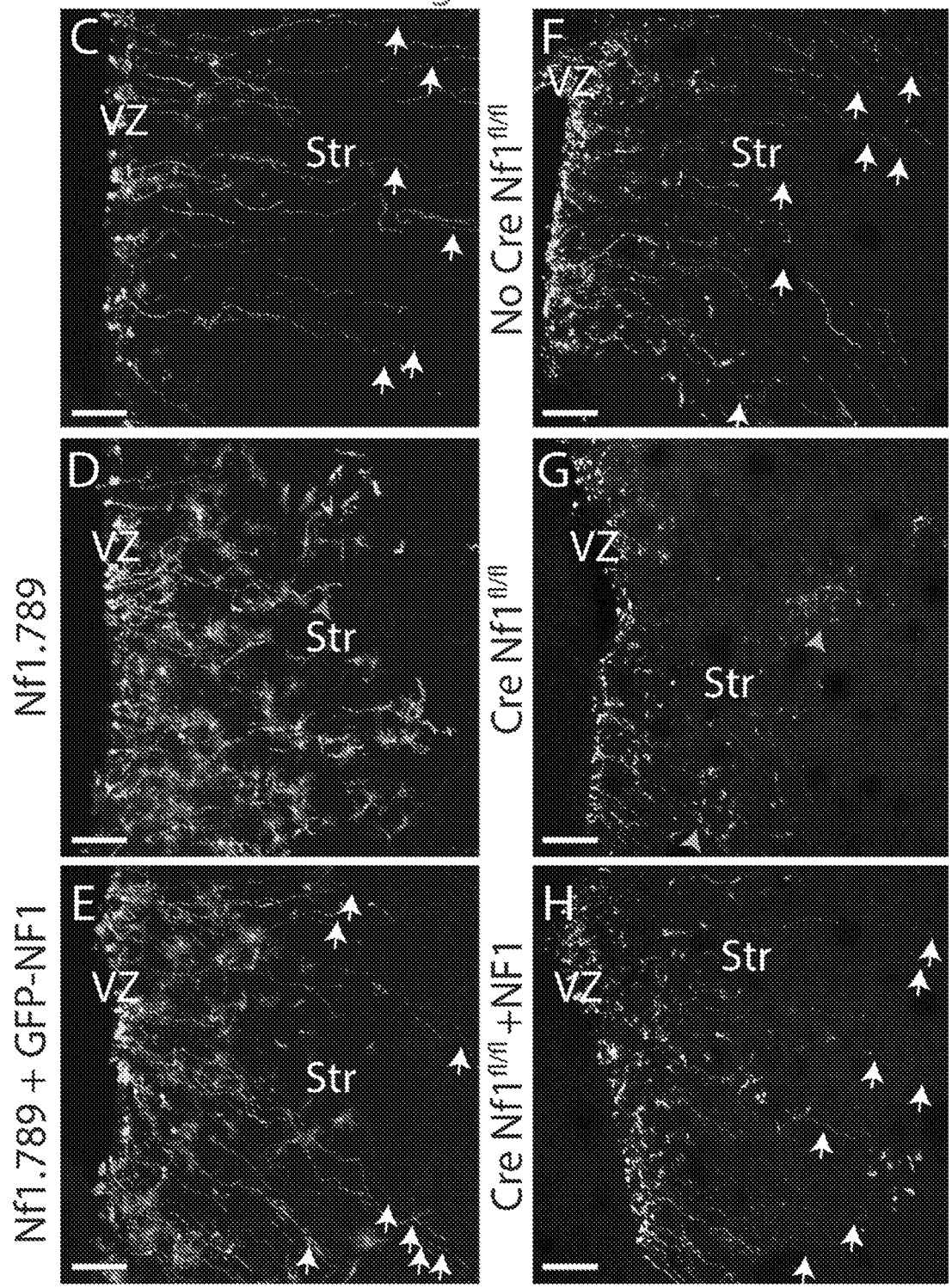
Figure 4:
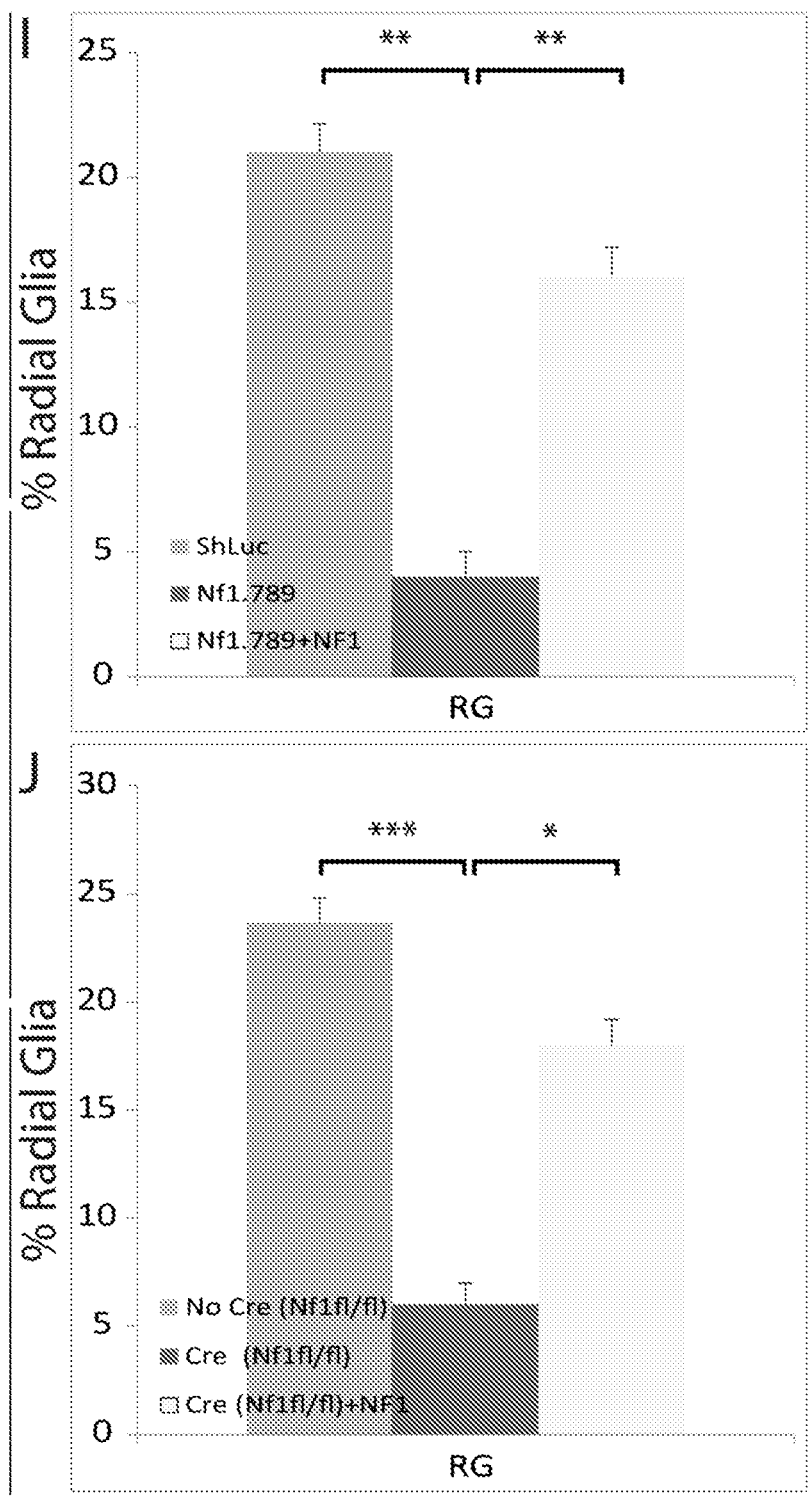

In regions where cell body density precludes definitive tracing of individual radial glia (FIG. 1E; FIG. 4H, 4V-W; FIG. 8G), stained sections (N=3 brains for each age group) were imaged along the VZ/SVZ region with at least two images per brain. For each brain within the region where 100 nuclear TagBFP2 positive cells were counted, the number of radial processes were counted.

Example 12

Double Electroporation

Initial electroporation of plasmids along with pBase was performed. Animals were returned to their cages and allowed to recover. Eight hours later, the animals received a second electroporation in the same ventricle of the second cohort of plasmids, including pBase.

Example 13

Pathology

After brains were harvested and fixed in 4% PFA overnight, tissue was embedded into paraffin and 5 µm coronal sections were collected on slides. Paraffin was removed and an H&E staining was performed prior to grading.

Example 14

Western Blot

Mouse forebrain neural stem cells i were nucleofected following the Lonza Amaxa Mouse Neural Stem Cell Nucleofector Kit (setting A-033) procedure. Equal plasmid concentrations were used in each group. The Clover-F group contained pCag hypBase-HA, pCag TagBFP2-3×Flag-nls PB, and pCag Clover-F PB plasmids. The Clover-F:T2a:V5-Erbb2 group contained pCag hypBase-HA, pCag TagBFP2-3×Flag-nls PB, and pUb Clover T2a v5 Erbb2 V664E PB plasmids. The Clover-F+V5-Erbb2 group contained pCag hypBase-HA, pCag TagBFP23×Flag-nls PB, pCag Clover-F PB, and pUb v5 Erbb2 V664E PB plasmids. After nucleofection the cells were grown for three days at 37□C. The cells were harvested by incubating them with accutase for 3 min at 37□C, resuspending them in an equal amount of media, and then centrifuging for 3 min at 300 rpm. The resulting pellet was then re-suspended in laemmli buffer and boiled for 15 min at 95□C. The protein concentrations were measured using a ThermoScientific Nano Drop.

Following SDS-PAGE separation and transfer onto nitrocellulose membranes, proteins were detected using the following antibodies: Erbb2 rb (1:1000), V5 ms (for v5 Erbb2 V664E, 1:1000), eGFP ck (1:10,000), Flag ms (for TagBFP-3×Flag-nls, 1:1000), and Actin ms (1:1000; detailed antibody information in Table 2). All secondary antibodies (Jackson Immunoresearch; HRP conjugated) were used at a 1:2500 dilution. Detection was accomplished by chemiluminescence using the BioRad ChemiDoc XRS Imaging System.

Example 15

Micro Magnetic Resonance Imaging

Ferritin electroporated mice co-electroporated with either EGFP-F or EGFP-Hras G12V were placed in a Bruker BioSpin 9.4T micro-MRI and serial images through the head were collected over the course of one hour.

Example 16

Nucleofection

Neural stem cell nucleofection was performed using the Nucleofector 2b device (Program A-33) with the Mouse Neural Stem Cell Kit according to manufacturer's recommendations (Lonza AG) with the exception being that the suggested amount of DNA input was increased to ~7 µg of each plasmid.

Example 17

Cell Dissociation

Sterilized dissection tools were immersed in 70% ethanol and placed in a laminar flow hood with at least 30 minutes of UV light exposure prior to use. Mice were euthanized in a CO2 chamber (per Cedars-Sinai IACUC Protocol #3507). After cervical dislocation, mice were decapitated using large sterile dissection scissors. Whole heads were placed into 50 mL conical tubes containing 70% ethanol on ice for five minutes (mice P4-P8) or ten minutes (mice >P8). Tubes were removed from ice and placed into the laminar flow hood.

Heads were removed from ethanol and smaller dissection scissors were used to cut the skin down the midline of the head. One cut was made at the snout, anterior to the olfactory bulbs, and another down the midline of the brain. Both hemi-sides of the skull were separated using forceps, leaving the brain exposed. The SVZ on the left side of the mouse brain (site of EP) was then sub-dissected using scissors and placed into a 10 cm petri dish containing 1 mL of media (as described in Cell Culture Methods below). Using a sterile utility razor blade, tissue was chopped for approximately 30 seconds or until pieces were 1 mm3 or smaller. Using a P1000, the cell suspension was carefully and slowly pipetted against the wall of the petri dish 5 times and then transferred into a 15 mL conical tube. Additionally, 1 mL of media was used to wash off the petri dish to pick up any cells left behind and placed into the collecting conical tube. Cells were spun down at 1350 rpm for 2 minutes. Supernatant was aspirated and the pellet was resuspended in 4-6 mL (depending on pellet size) of accutase (Millipore SCR005) and incubated at 37° C. in 5% CO2 for 10 minutes. During this incubation, tubes were inverted approximately 5 times, disrupting the cell suspension, every 3 minutes. An equal volume of fresh media was then added to neutralize the accutase and cells were spun down at 1350 rpm for 3 minutes. Supernatant was then removed and pellets were resuspended in fresh media and placed into T75 cm2 flasks coated with CELLstart (Life Technologies A10142-01).

Example 18

Cell Culture

Cells were grown in media containing Neurobasal-A Medium (Life Technologies 10888-022) supplemented with B-27 without vitamin A (Life Technologies 12587-010), GlutaMAX (Life Technologies 35050-061), Antibiotic Antimycotic (Life Technologies 15240-062), Epidermal Growth Factor (EGF, Sigma E9644), heparin (Sigma), and Fibroblast Growth Factor (FGF, Millipore GF003). Media was changed every two days.

Example 19

FACS

Once harvested cells reached approximately 80% confluency, media was removed and T75 cm2 flasks were passaged with 2 mL of accutase at 37° C. in 5% CO2 for 3 minutes. Accutase was neutralized with 2 mL of media and cells were spun down at 1350 rpm for 3 minutes. Supernatant was removed and cells were resuspended in 2 mL of fresh media, using a P1000 in order to disrupt the cells in a careful yet vigorous manner. In increments of approximately 200 µL, cells were filtered through a 100 µm filter. The collected filtrate was then passed through a 70 µm filter. This filtrate was then placed on ice. Cells were then FACS sorted for GFP with tight gates making sure only the cells highly expressing GFP were collected, indicative of either membrane UFEKPB or HRAS-GFP-PB plasmid expression. Cells were collected into fresh media kept cold and on ice. Once all cells were sorted, the collected cells were pelleted and placed into new T75 cm2 flasks coated with CELLstart.

Example 20

Tumor Cell Line Targeted Sequencing

RNA from each cell line was reverse transcribed in a "one step" reaction with gene-specific primers according to manufacturer's instructions (Kapa Biosystems). These primers and/or internal primers were used for Sanger sequencing. Multiple, independent rounds of reverse transcription and sequencing were used to confirm the individual mutations. Primer sequences are available upon request.

Example 21

Acute Double Electroporated Cell Culture

At P8, double EP mice VZ/SVZ were dissociated as described above. Cells were placed in T75 cm2 flasks coated with CELLstart with media supplemented with growth factors for two days to allow sufficient time for cells to settle. Next, samples were passaged (as described in FACS) and plated onto glass coverslips, in media without supplementing EGF, heparin or FGF. Media was changed every two days and coverslips were fixed at one week post removal of growth factors.

Example 22

Mouse Cell Culture Immunostaining and Quantification

Three glass coverslips were used for each animal sample (Control, Tumor #1, Tumor #2, and Tumor #3). Images were taken on the Nikon AIR confocal, using the 20× objective for all samples. The same laser settings were used for all samples. Being that all cells were sorted and GFP+, 100 cells were then counted for, based on their expression of TagBFP-V5-nls-PB. Out of these 100, cells were then counted for being either PDGFRα positive, Sox10 positive, or both PDGFRα and Sox10 positive. For double electroporated experiments, coverslips were stained for each animal per cell marker for V5, GFP, HA and either Dcx, Gfap, or Olig2 (one week samples) and Pdgfra (two week samples). 5 random fields per animal (4 animals A, B, C and D) at 1 week (staining for Olig2 and Dcx) were chosen for quantification. For control cells, the % of Bgla-Ha-positive and marker-positive cells which were negative for TagBFP2nls-V5 was determined. For Hras G12V cells, the converse percentage of TagBFPnls-V5-positive, marker-positive, Bgla-HA-negative cells was determined.

Example 23

Human Cortical Progenitor Cell Culture and Nucleofection

HuNPCs (human neural progenitor cells) from fetal cortex (G010 cell line) were a generous gift from the Svendsen Laboratory. Methods to grow HuNPCs have been described and conform to National Institute of Health and Cedars-Sinai Medical Center guidelines. Briefly, HuNPCs were expanded as neurospheres in media containing Stemline (Sigma S3194) supplemented with Epidermal Growth Factor (EGF, Sigma E9644), Leukemia Inhibitory Factor (Millipore LIF1010) and Antibiotic Anti-mycotic (Life Technologies 15240-062). Spheres were dissociated to single cells for nucleofection with Hras, Kras or UFEK (Control) plasmids. After nucleofection, growth factors were removed and media was supplemented with B-27 (Life Technologies 12587-010). Cells were grown as monolayers for 2 weeks and then fixed with 4% paraformaldehyde (PFA). Human neural progenitor cell nucleofection was performed using the Amaxa Nucleofector 2b device (Program A-33) according to manufacturer's recommendations (Lonza AG). Counts were done by an observer blind to the experimental manipulations.

Example 24

Tumor Cell Transplantation 100,000 EGFP+ purified tumor cells were transplanted into P3 CD1 mice as per previously described method. Briefly, purified EGFP+ cells were liberated from monolayer cultures using accutase, spun down, and collected in PBS with fast green dye. This solution was then microinjected into the forebrain of perinatal CD1 mice.

Example 25

Stable Transgenesis of Ventricular Zone Cells

To evaluate the ability of transposition to mediate stable transgene expression, plasmids harboring CAG-driven enhanced green fluorescent protein (EGFP) flanked by terminal repeats (PB-TR) that enable the genomic integration by pBase were expressed in the mouse left lateral ventricle using electroporation (EP) at postnatal day 2 along with an electrode orientation to target the striatal wall of the left ventricle (FIG. 1A-B). At 6 months post-EP, a large number of cells showed stable EGFP expression, while the EP of an episomal plasmid lacking PB-TR resulted in a 10 fold reduction in the number of stably fluorescing cells, indicating that pBase transposition facilitates stable transgenesis (FIG. 1C).

Mouse brains were analyzed four hours post-EP to acutely identify the electroporated (EP-ed) cells, most of which were radial glia (RG)—a bonafide NSC population (Rakic, 2003), and a small fraction expressed the progenitor markers Ascl1 and/or Olig2, but no cell was both Ascl1+ and Olig2+(FIG. 1D-E). Two days after EP, many cells remained Vimentin+ RG, possessing prototypical basal-apical polarity and a VZ-anchored cell body with a basal process >100 μm (FIG. 1F-$G_4$, FIG. 8A). Over six months, these EP-ed cells collectively gave rise to olfactory bulb neurons (FIG. 1H, J), OPCs (FIG. 1K, Sox10+/Olig2$^+$ cells morphologically identifiable as multipolar glia exhibiting fewer processes when compared with astrocytes as seen in FIG. 8B-$B_3$), oligodendrocytes (FIG. 1K-L), astrocytes (FIG. 1M; Aldh111$^+$/Gfap$^+$ glia with a dense cloud of processes as displayed in FIG. 8C-$C_3$), and ependymal cells (FIG. 1N; i.e. VZ-located, apically multiciliated, cuboidal cells). Some RGs remained in the VZ, demonstrating their long-term self-renewal or quiescence (FIG. 1I). The Inventors did not observe any hyperplasia or tumor formation in stably EP-ed cells (e.g. containing only the stably inserted TagBFP2 nuclear reporter or EGFP; FIG. 1I, J.B., R.L., data not shown).

Example 26

Tumorigenesis Initiated by Electroporation of Single Oncogenes

To assess the ability of this methodology to generate glioma, the Inventors EP-ed the following constitutively active oncogenes, which have been identified as driver mutations in previous models or in patient tumors: Erbb2-V664E, Hras-G12V, Kras-G12V, and Pdgfra-D842V.

Several strategies were employed to unambiguously visualize targeted cells. For Erbb2 plasmids, the Inventors co-expressed the mClover green fluorescent protein using a self-cleavable 2A peptide sequence (FIG. 9A-B). Hras-G12V and Kras-G12V genes were fused with EGFP (FIG. 9A), and Pdgfra-D842V was constructed without a reporter or tag (FIG. 9A). The control gene was a fusion of EGFP with the CAAX box found in Hras C-terminus, which results in membrane labeling (FIG. 9C). This membrane-targeted EGFP was also used for visualization of Pdgfra D842V by co-EP of both plasmids.

Figure 2:
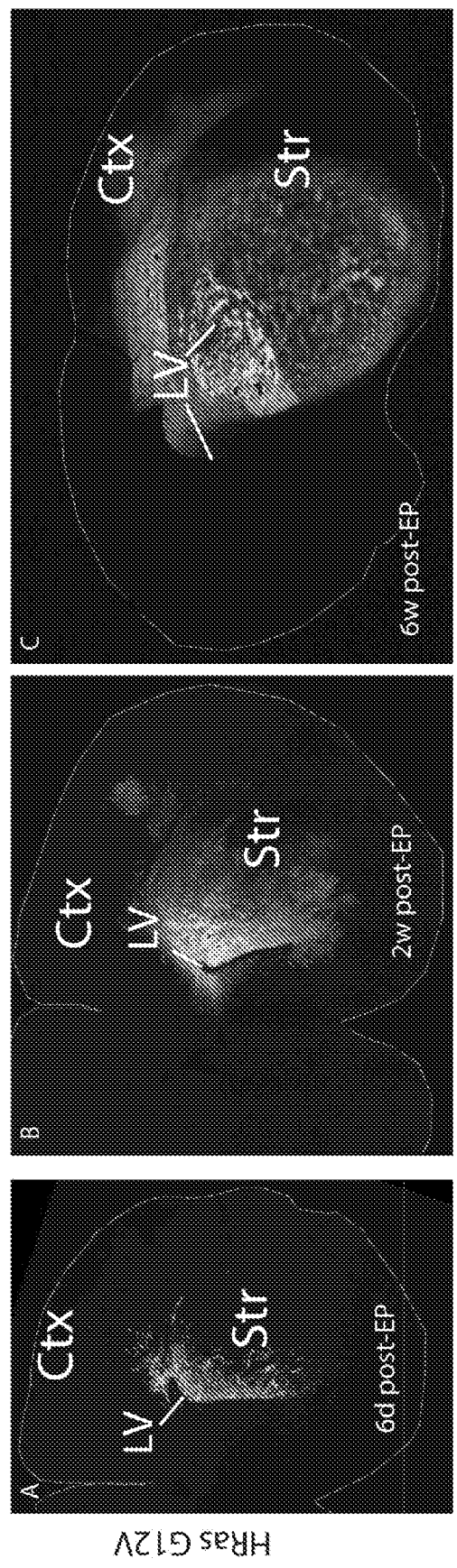
FIG. 2. Tumor progression and pathological findings in EP-ed mice.
Figure 2:
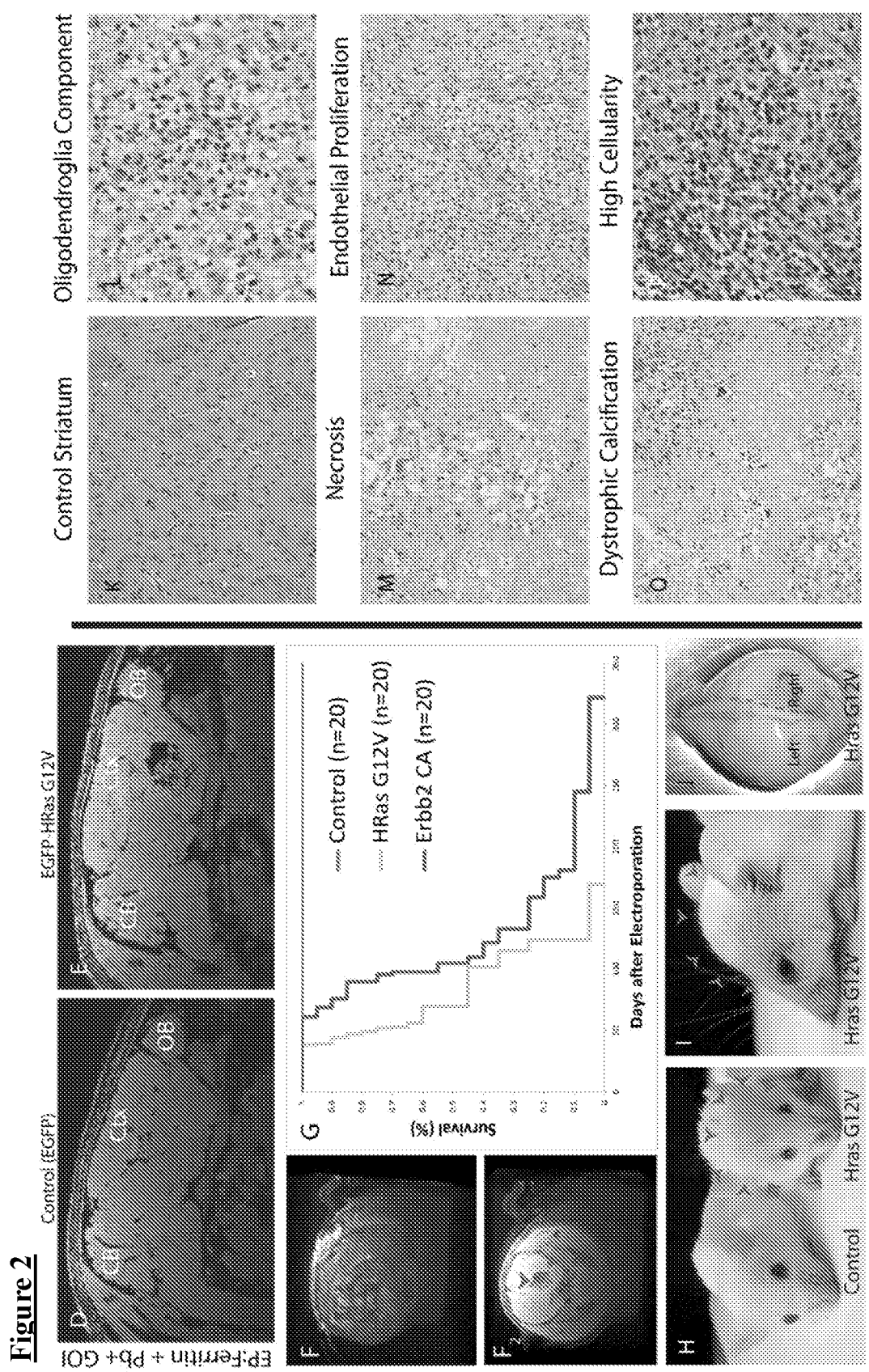
Figure 3:
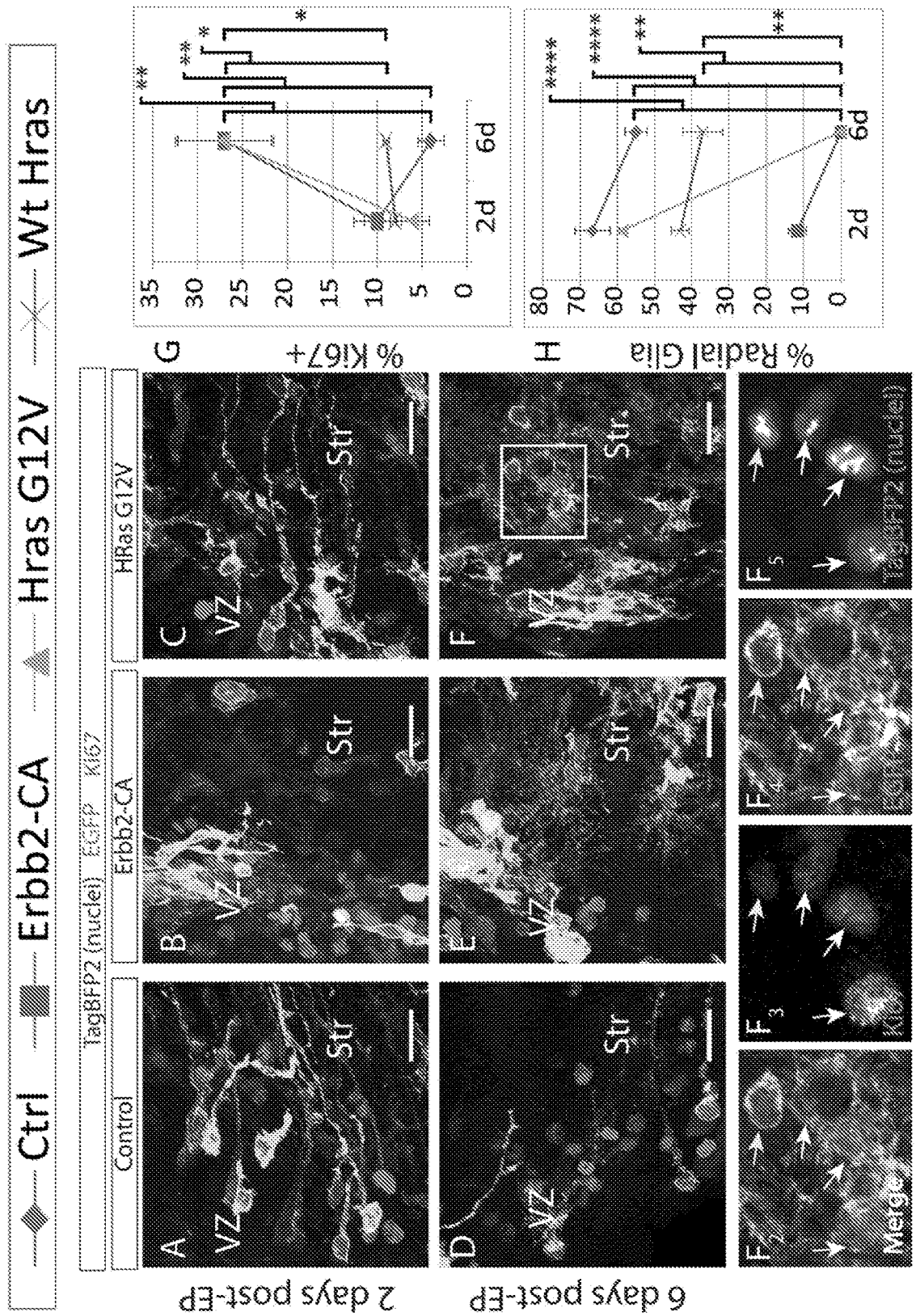
FIG. 3: Somatic mutation rapidly depletes RG and expands tumor cells.
Figure 3:
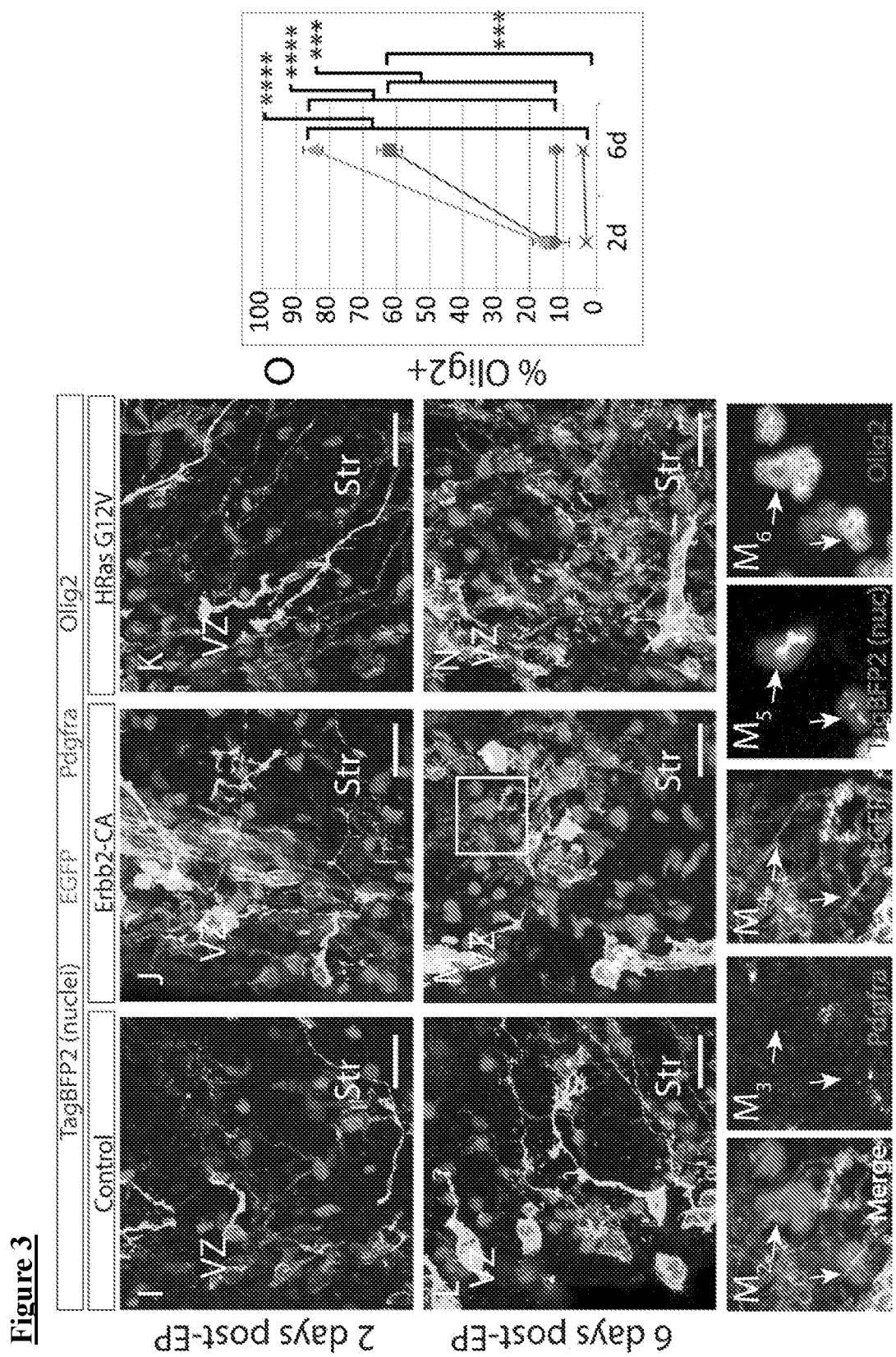
Figure 3:
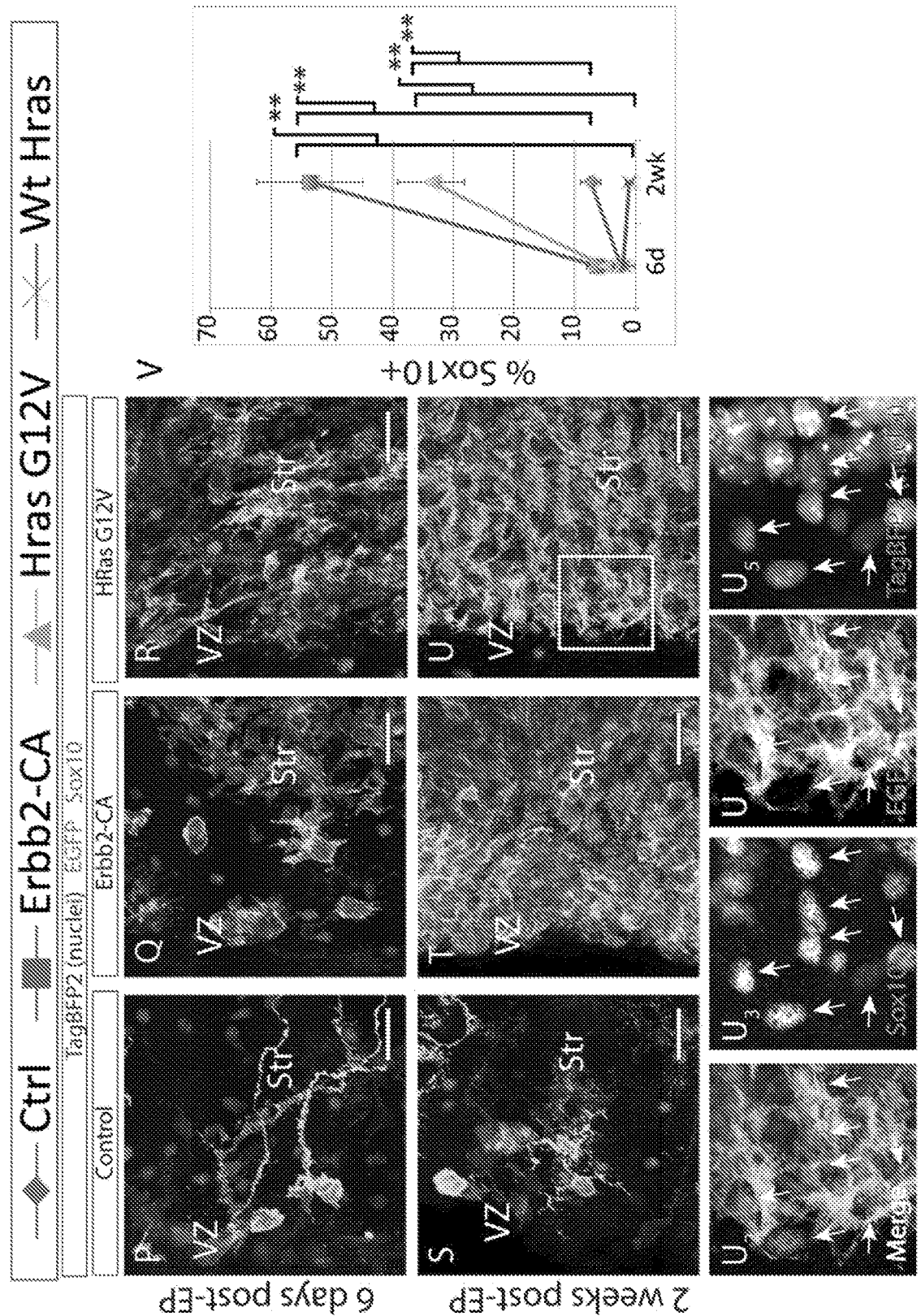

Stable expression of Erbb2-V664E or Hras-G12V oncogenes led to the rapid development of hyperplasia between 6 days and 2 weeks (FIG. 2A-B; FIG. 9DE). Though starting as small populations of VZ cells, the EGFP$^+$ cells became highly infiltrative and tumors occupied a significant proportion of the forebrain volume by six weeks (FIG. 2C; FIG. 9F). Electroporation of Kras and Pdgfra mutations also resulted in the formation of tumors (FIG. 9G-H). Co-expression of oncogenes with a ferritin-expressing plasmid permitted cell growth to be tracked in live animals using MRI. Results showed tumor growth 3 weeks post-EP specifically in the left hemisphere at the site of EP (FIG. 2D-$F_2$). Importantly, wild-type Hras or Erbb2 overexpression did not exhibit noticeable increases in proliferation or loss of apicobasal polarity (FIG. 9K-L). Further, no mice EP-ed with control plasmids developed tumors, indicating that pBase expression or random genomic insertions of plasmids are not sufficient to initiate significant tumorigenesis under these conditions. These findings show that pBasemediated stable integration of a single constitutively active Ras pathway mutation in the VZ niche can initiate tumors.

Hras G12V and Erbb2-CA driven tumors were 100% penetrant (FIG. 2G). The majority of Hras G12V animals showed hydrocephalus and doming of the skull and reached terminal endpoint within ~200 days, whereas control animals (i.e. EP-ed with membrane EGFP and transposed with pBase) did not show any abnormal symptoms or shortened lifespan (FIG. 2G-I). The Inventors observed overgrowth of the left hemisphere, abnormal vascularity, and cortical thinning in tumor-bearing animals (FIG. 2J). The Hras-G12V tumors were graded by a clinical neuropathologist according to World Health Organization criteria and found to possess the hallmarks of high grade anaplastic glioma by pathology—notably an oligodendroglioma component as demonstrated by the artifactual "fried egg" appearance of tumor cells, necrosis, endothelial proliferation, calcification, and high cellularity (FIG. 2K-P). Erbb2-V664E animals exhibited similar pathological features (FIG. 9M-R).

All Ras and Erbb2 mutations were pathologically classified as high grade glioma. However, even littermates—treated identically—could exhibit divergent pathologies within the Grade III and IV subtypes. Specifically, tumors were diagnosed as anaplastic astrocytoma, anaplastic oligodendroglioma, anaplastic oligoastrocytoma, or glioblastoma multiforme.

Example 27

Premature Radial Glia Depletion and Progenitor Hyperplasia Through Ras Hyperactivation Employing a counting frame-based system for quantification (FIG. 10A-B), the Inventors observed that the EP-ed VZ cells rapidly lost their RG morphology and increased proliferation by 6 days (FIG. 3A-H). This conversion of morphology happened in all Hras, Pdgfra and Kras electroporations, suggesting that this effect is the result of the consistent hyperactivation of Ras that is commonly associated with gliomagenesis (FIG. 3G; FIG. 9G-J). This morphological change was significantly correlated with increases in Olig2 expression, indicating potential lineage restriction (FIG. 3I-O).

The Inventors employed Sox10 immunolabeling to investigate oligodendrocyte lineage restriction as it is specific for this class of cells in the normal brain. From 6 days to 2 weeks, the number of Sox10+/EGFP+ tumor cells rapidly increased as the tumor progressed, indicating an increase in OPCs within the growing tumor (FIG. 3P-V).

The acute changes in expression of oligodendrocyte cell markers were replicated using cerebral cortex-derived human neural progenitor cells (hNPCs). hNPCs EP-ed with Hras or Kras mutants became compact in nature and upregulated Olig2 and downregulated the astrocyte lineage marker GFAP, while control hNPCs retained GFAP expression and a spindle shaped morphology reminiscent of RG in vitro (FIG. 10C-F).

Ras hyperactivation often results from the loss of Nf1 activity that frequently occurs in glioma patients. To test whether Nf1 deficiency mirrors Hras phenotypes, the Inventors adapted two methodologies for use with the Inventors' EP technique. First, the Inventors knocked down Nf1 in EP-ed cells using the recently reported miR-E shRNA technology (FIG. 4A). In addition, the Inventors created a strategy to EP Nf1 floxed mice with a custom-made FlEx reporter plasmid and Cre (FIG. 4B).

In validating miR-E targeting plasmids, western blot analysis confirmed that all five candidate Nf1 shRNA sequences efficiently knocked down their cognate sensor EGFP in transfected N2a cells more strongly than a previously characterized shEGFP (FIG. 11A-B). Nf1.789 (shNf1) was used in all further experiments because its effect could be rescued by a codon-optimized human NF1 cDNA; FIG. 11C-D). When the Inventors EP-ed shNf1 and sensor EGFP, only a few "escaping" EGFP$^+$ RGs remained, while a large increase in EGFP-striatal cells could be seen in these groups (FIG. 11E-E$_4$). Control shRNA against firefly luciferase (luc. 1309 heretofore "shLuc") did not decrease sensor EGFP expression or change the overall distribution of EGFP cells (FIG. 11F-F$_4$).

The Inventors then EP-ed littermates with shLuc, shNf1, or shNf1+human Nf1. After six days, shLuc control mice retained the stereotypical RGs while shNf1 mice displayed markedly more striatal glia and a loss of RGs. These shNf1 phenotypes were rescued by coexpressing the human NF1 cDNA (FIG. 4C-E). Immunostaining for NF1 protein confirmed the resistance of the human NF1 cDNA to shNf1 after coEP of both (FIG. 11G-G$_3$). Notably, the human NF1 signal was enriched in VZ cells, but this episomal cDNA appeared to be rapidly diluted in the escaping, proliferative glial populations (FIG. 11G-G$_3$). The radial glia depletion phenotypes were replicated in the floxed Nf1 mice EP-ed with Cre recombinase (FIG. 4F-G), and the loss of RGs was again attenuated by co-expressing human NF1 (FIG. 4H). Both shNf1EP-ed and Cre-recombined Nf1 mice showed a significant reduction in the number of RGs (FIG. 4I-J). These data suggest that both Ras hyperactivation and Nf1 reduction in RG leads to the cell autonomous depletion of RGs.

In addition to creating focal, genetic mosaic models for cell tracing, the Inventors used this technology to test if the depletion of RGs is evidence of a change in neural stem cell potential. EP-ed plasmids are preferentially taken up by the RGs undergoing M-phase of the cell cycle. Because the VZ cell cycle is roughly 12-18 hours, the Inventors hypothesized that the Inventors could electroporate the same animal twice with different plasmids, eight hours apart, and expect to generate two genetically different cohorts of RGs (FIG. 12A). To mitigate the possibility of double positive cells, the Inventors added Cre recombinase in the first round of EP to inactivate any floxed-Hras plasmid that might enter the same cell during the second EP (FIG. 12A). After performing double EP with HA-tagged, nuclear beta-glucosidase+Cre in the first EP (control group) and nuclear TagBFP2 (TagBFP2nls-V5)+Ollas/Flag-epitopetagged Hras G12V in the second EP (HRas group), the Inventors dissociated EP-ed cells from four animals, grew them in culture with growth factors for two days to permit expansion and clear debris, and then re-plated cells on coverslips without growth factors to induce differentiation (FIG. 12A). As with the Inventors' in vivo experiments, a significant increase in Olig2+ cells was observed in the Hras group (FIG. 12B-C). After seven days, the absolute number of Olig2+ cells in the Hras group was almost 17-fold higher (290±141 Olig2+ cells in Hras-G12V versus 17±7 Olig2+ cells in controls; n=4). Neuronal differentiation was almost completely abolished in Hras cells, as the Inventors found a total of 4 doublecortin-positive neuronal cells from 4,505 TagBFP2+/Hras-G12V cells sampled across four cell lines (FIG. 12B, D). Astrocytic differentiation was decreased in Hras-G12V cells (64.8±12.7% compared to 48.6±16.4% GFAP cells; FIG. 12B, E). In agreement with the disappearance of OB neurons in vitro, olfactory bulb neurogenesis appeared to decrease in vivo in Hras-G12V and Erbb2 groups (FIG. 12F-H). These data show that Hras hyperactivation in NSCs prevents neuronal lineage specification and favors glial lineage specification. Collectively, these results suggest that the NSC character is lost acutely during a RTK/Nf1/Ras-mediated expansion of glioblastic tumor cells.

Example 28

Characterization of PiggyBac Tumor Propagating Cells

Figure 5:
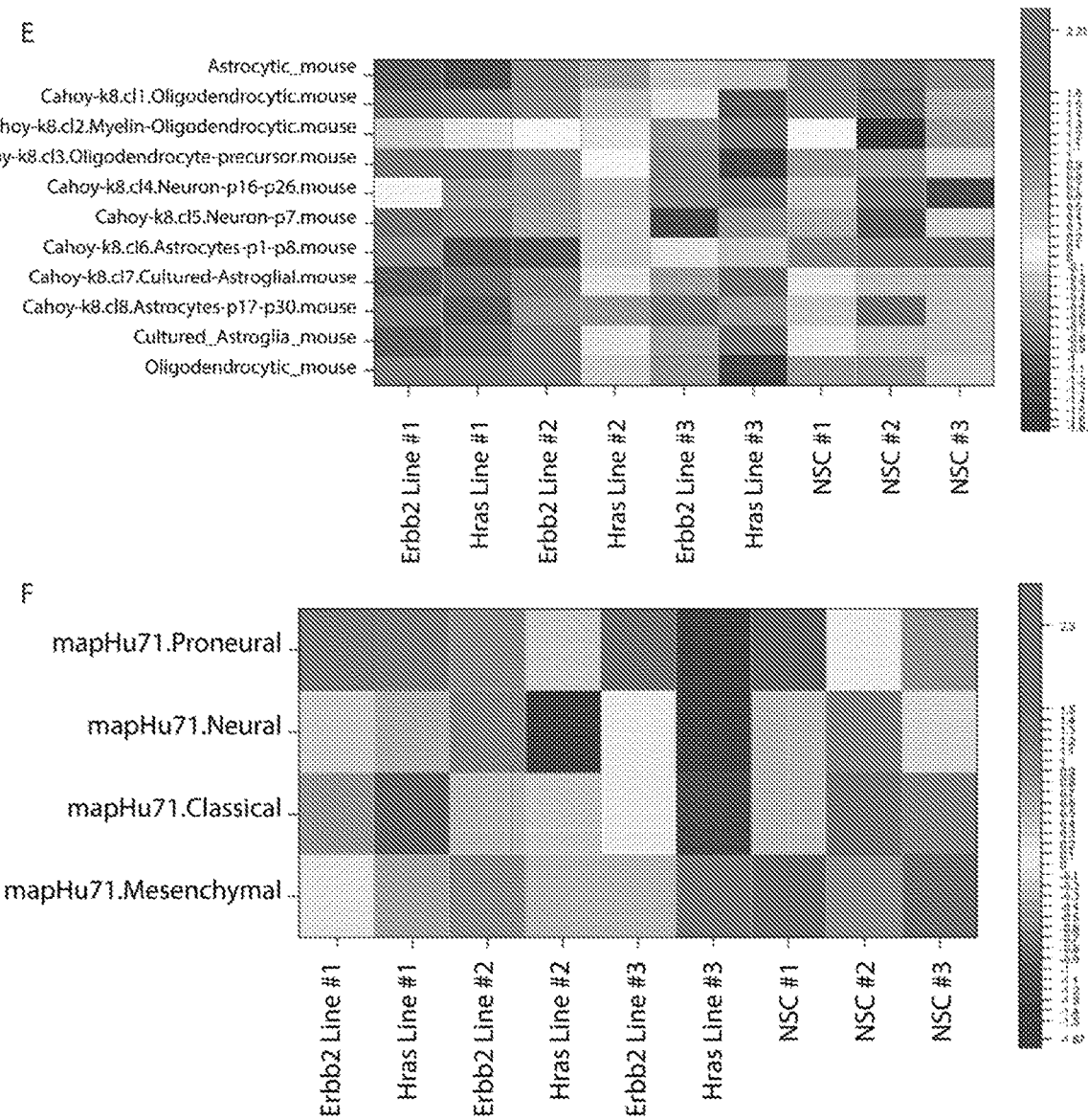
FIG. 5. Isolation and microarray analysis of highly pure populations of tumor cells.

Three Hras+ and three Erbb2+ tumors from different animals were dissociated and fluorescently sorted to give pure EGFP+ populations (FIG. 5A). The Hras tumor cell lines all highly expressed Pdgfra and Sox10 (at least 80%), though one Hras cell line had significantly less Pdgfra+, Sox10+ cells (FIG. 5B-D). This Pdgfra/Sox10 co-expression was not seen in "sibling", control cells that were isolated from EGFP-expressing, pBasetransduced animals (FIG. 5B).

RNA isolated from the six Hras-G12V and Erbb2V664E cell lines and control NSCs was analyzed by microarray. Single-sample gene set analysis (GSEA) of cell lines using the brain transcriptome database and the glioma subtype signaturesrevealed that the tumor cell lines were highly heterogeneous when viewed as individual lines (FIG. 5E). Erbb2-1, Erbb2-2 and Hras-1 were enriched for oligodendroglial signature while Erbb2-3, Hras-2 and Hras-3 had a more astroglial profile (FIG. 5E). Three oligodendroglial lines were found to contain more proneural/neural signatures while three astroglial lines were more mesenchymal (FIG. 5F).

Given that the Hras lines and Erbb2 lines were derived from same birthdate animals (i.e. EP-ed during the same surgery) from the same respective DNA mixes (i.e. containing either Hras or Erbb2 for the respective groups), the Inventors suspected that the divergence of expression profiles within tumor evolution in each group might be partially attributed to the stochastic acquisition of secondary mutations, which is suggested by several recent studies reporting that gliomas exhibit high intratumoral heterogeneity. In screening several tumor suppressors, the Inventors observed that all tumors harbored at least one secondary mutation in Trp53, p16, or p19, indicating a potential mechanism for their heterogeneity (FIG. 13A). Several of these Trp53 mutations (A135V, V170M, V213M) have also been observed in other mouse models of glioma or in human glioma.

To confirm that EGFP+ cells are truly tumorigenic, the Inventors performed transplantation of 100,000 tumors cells into naïve P2 mice and saw invasive tumors similar to the initial primary tumors marked by high Sox10 and Olig2 expressions (FIG. 13B-D).

Example 29

Etv5 is Required for Ras-Mediated Gliomagenesis

Figure 6:
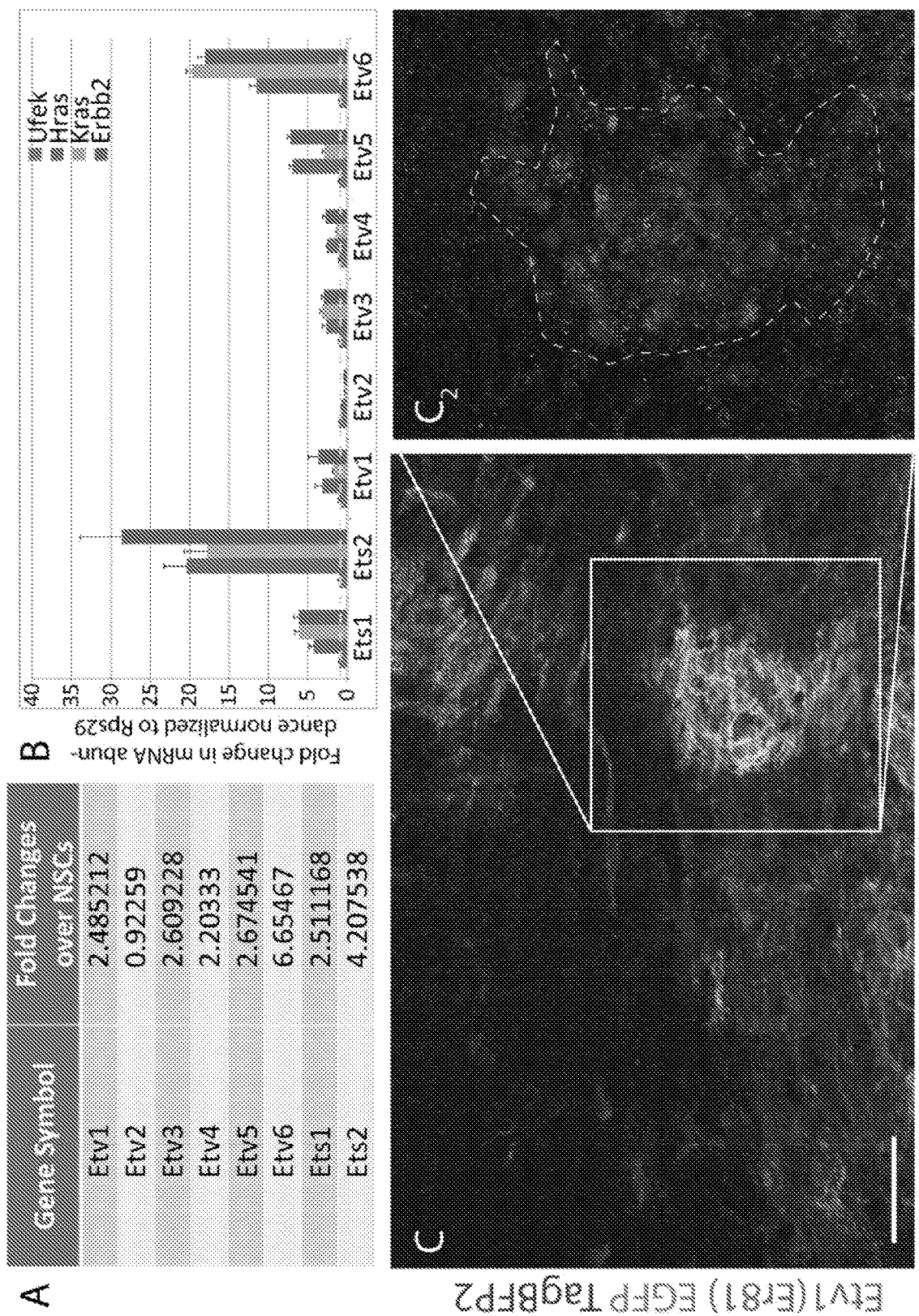
FIG. 6. Ets-family transcription factors are upregulated in glioma and regulate tumor cell phenotypes.
Figure 6:
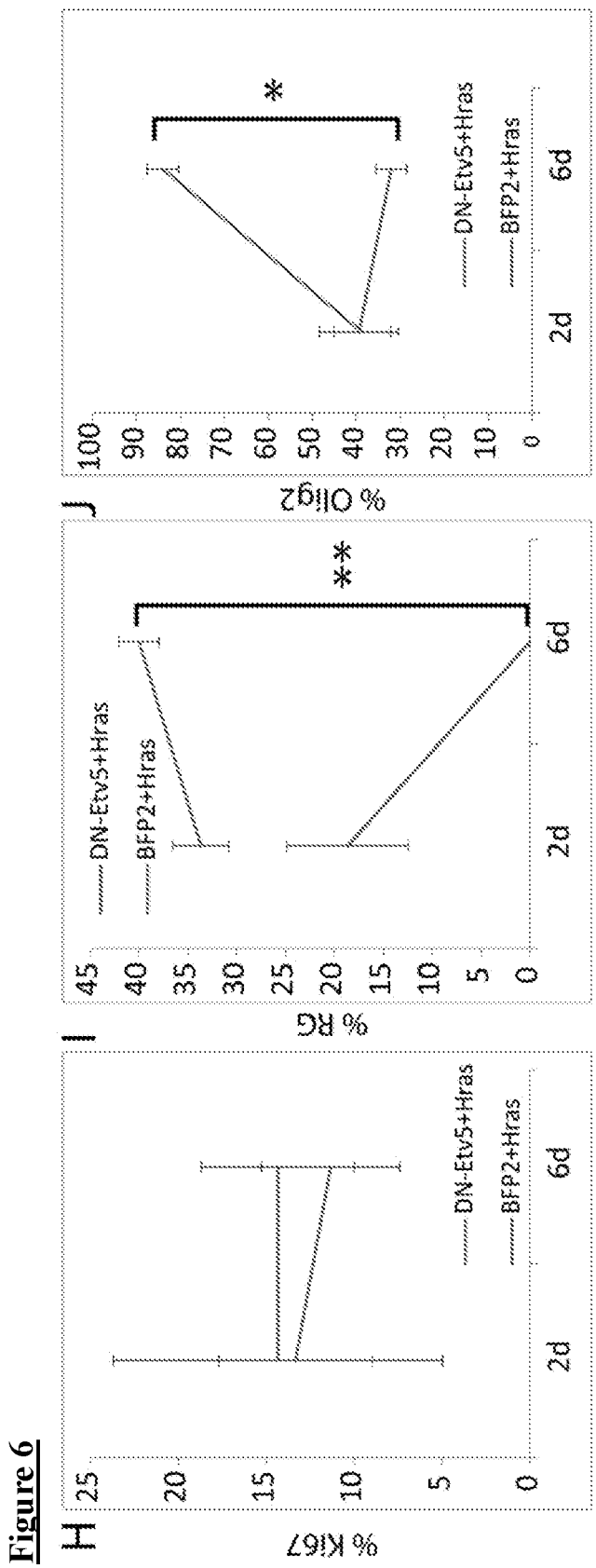

Recently, Etv5 has been reported to be critical for perinatal gliogenesis. A preliminary microarray screen showed that many members of the Ets transcription factor family, and Pea3 subfamilies of the Ets-family, were upregulated in the tumor cells when compared with NSCs (except Etv2, which does not appear to be expressed in the brain; FIG. 6A; FIG. 14A). The upregulation of Ets-family was confirmed by qRT-PCR across Kras, Hras, and Erbb tumors (FIG. 6B). Using a well-characterized Etv1 (aka Er81) antibody that efficiently labels deep-layer cortical neurons (A.A., data not shown), the Inventors observed the upregulation of Etv1 protein in tumor cells (FIG. 6C-C$_2$).

Because of the pleiotropic function of Ets factors in the brain, and due to the fact that so many members of the Ets family were simultaneously upregulated, it would be difficult to use shRNA or floxed mice to assess Ets function in tumorigenesis. Thus, the Inventors engineered a dominant-negative Etv5 (DN-Etv5) which consists of TagBFP2 fused to the DNA binding domain of Etv5. DN-Etv5 cross-reacts with other members of the Ets family to suppress their transcriptional activities by binding the GGA(A/T) consensus site. Initial attempts at co-EP of Hras G12V and DN-Etv5 indicated that cells expressing DN-Etv5 did not transform at a high rate but "escaping" Hras-G12V cells quickly out-competed DN-Etv5+ populations (R.L., data not shown). The Inventors then constructed a bicistronic plasmid containing EGFP-Hras G12V and TagBFP2-DN-Etv5 separated by a P2A element (FIG. 6D). The Inventors substituted Etv5 DNA binding domain with three Flag epitopes and a nuclear localization sequence (nls) to construct the control plasmid (FIG. 6E). A constitutively active Etv5-DBD-VP64 and a full length TagBFP5Etv5 were also generated (FIG. 14B). Proper function of the P2A element was confirmed by the appropriate membrane localization of Hras and nuclear localization of TagBFP2-DN-Etv5 (FIG. 14C). Further, a SRE-driven dual luciferase assay validated that Hras G12V activity in the P2A-containing plasmid was equivalent to coexpressed Hras G12V (FIG. 14D). Moreover, co-expression of these plasmids with Pea3-driven luciferase plasmid revealed that Hras upregulated Pea3 luciferase activity, and that co-expressed DN-Etv5 (i.e. Hras and DN-Etv5 in separate plasmids) or bicistronic Hras/DN-Etv5 efficiently reduces this increase (FIG. 14E). Further, Pea3-driven luciferase activity was increased by Etv5 overexpression or more markedly by Etv5-VP64 expression (FIG. 14E).

While bicistronic TagBFP-3×Flag-nls/Hras G12V rapidly generated proliferative hyperplasias, electroporation of bicistronic DN-Etv5/Hras G12V resulted in an EGFP+ population that resembled the normal, control EGFP EP-ed brains and failed to generate tumors (FIG. 6F-G). There was no evidence of gross hyperproliferation, RG depletion, or the increase in Ki67+ proliferating cells or Olig2+ cells in the DN-Etv5 containing group (FIG. 6H-J). At 3 weeks post-EP, DN-Etv5 animals had no hyperplasia and no tumor, which contrasted with the 3Flag-bearing littermates (FIG. 7A-B). The overall number of cells in DN-Etv5 mice was still comparable to those seen in six month controls (e.g. FIG. 1I). DN-Etv5 animals survived well beyond 8 months, whereas the control group (TagBFP23Flag-nls-P2A-Hras) died (FIG. 7C).

Figure 7:
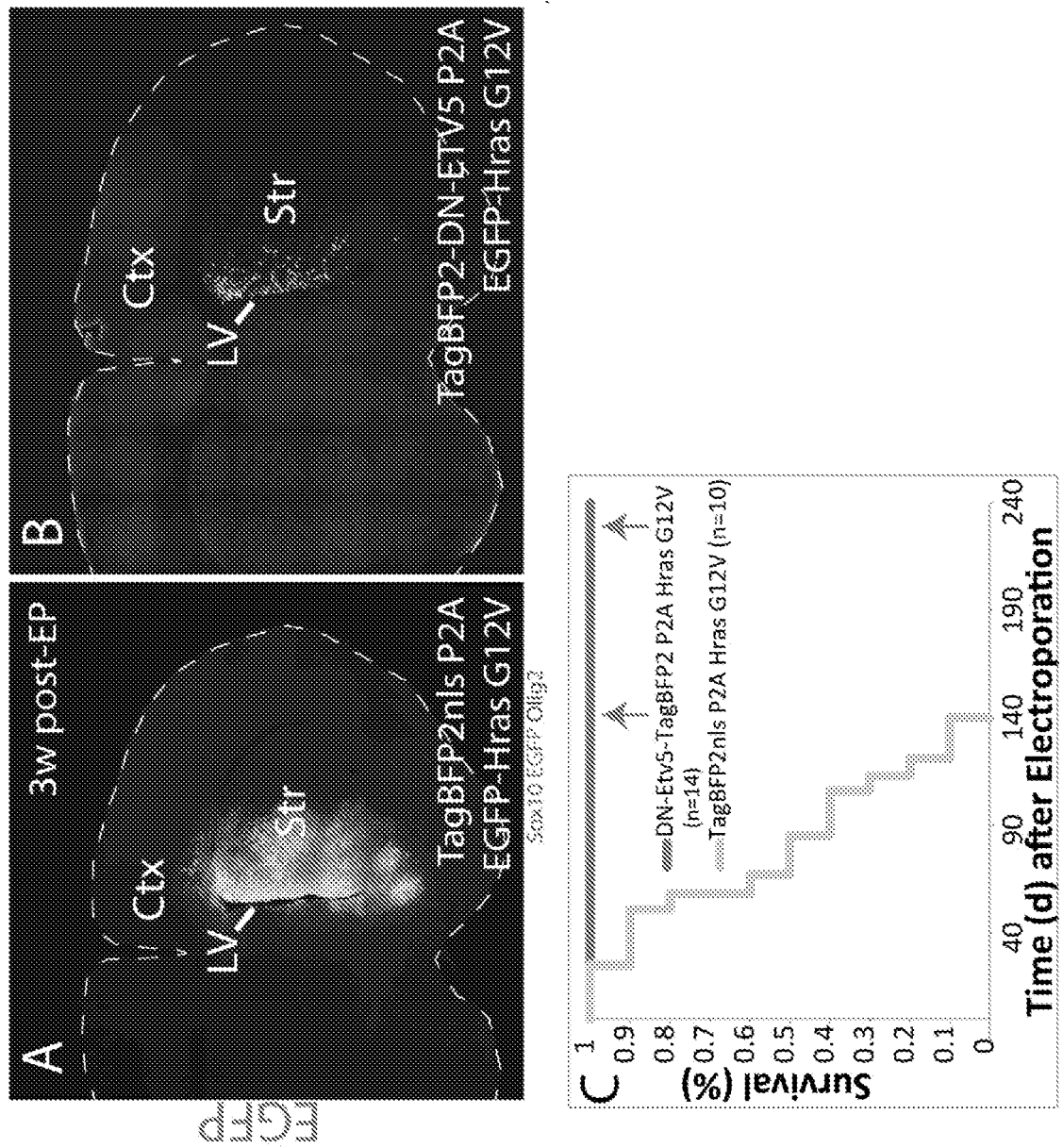
FIG. 7. Ets inhibition blocks tumor formation and prevents morbidity in Hras G12V mice.

The presence of large cohorts of EGFP+ cells in these long-lived DN-Etv5 mice argues against non-specific cytotoxicity (FIG. 7D). Histology of these animals did not yield evidence of tumor but the Inventors did observe numerous hypertrophic astroglia akin to those seen in episomal Hras G12V animals (J.B., data not shown). These hypertrophic glia did not express Sox10 or Olig2, but instead expressed astrocyte markers AldoC and Aldh111 and had an astrocyte-like morphology (FIG. 7E-$F_2$).

Example 30

Discussion

The Inventors combined postnatal EP with piggyBac transposition to model glioma by generating somatic transgenic mutants. Through the ability to rapidly model several glioma driver mutations, the Inventors identified that Ras pathway glioma requires Ets family transcription factor activity in order to transform mutation-harboring VZ populations into de facto tumors.

Using the Inventors' modeling technology with defined temporal and spatial transgene expression, the Inventors demonstrate that somatic Ras hyperactivating mutations (i.e. Ras mutations, RTK mutations, or Nf1 LOF manipulations) in VZ populations cause a rapid (<6 days) depletion of NSCs and a massive expansion of tumor propagating glial progenitors. Such phenomena would difficult to observe in traditional mouse models. For example, tamoxifen-induced recombination in genetically engineered mouse models happens over days in an organ-wide population of cells and often requires multiple, staggered injections, complicating the ability to identify the very first cells that might rapidly undergo transformations. Nevertheless, additional studies in the Inventors' model will be necessary to rigorously lineage trace these diverse VZ populations to see which of the initial populations (i.e. RG, Ascl1+, and/or Olig2+) will eventually contribute to the tumor bulk and, therefore, whether the depletion of RG is directly tied to progenitor expansion.

The molecular mechanisms of the perinatal switch from neurogenesis to gliogenesis has been an active area of investigation over the past decade. This field of inquiry has great importance due to the underlying glial nature of tumor propagating cells. Nf1 ablation was shown to promote proliferation of immature astroglial progenitors while diminishing neuronal differentiation. Further, alterations in neurosphere behavior have been observed in conditional Nf1 knockouts in a region-dependent manner. Interestingly, ERK inhibition is able to rescue cell fate specification in biallelic Nf1 inactivated animals by preventing transitamplifying progenitor cell expression of Olig2. Of particular note, it was recently reported that Mek activity is critical in regulating the neuron/glia fate switch in cortical progenitors as these knockouts demonstrated markedly diminished gliogenesis. The Inventors' findings further extend these previous findings by demonstrating Nf1/Ras function in NSCs to regulate their maintenance. Specifically, Ras hyperactivity due to direct mutation, Pdgfra or Erbb2 mutation, or through Nf1 knockdown or knockout, all result in RG depletion. However, unlike Nf1 mutations, direct Ras mutations are very rarely observed in glioma so it will be important to employ other mutations and/or combinations of mutations to see if these results can be generalized.

During the developmental gliogenic switch, Etv5 is the only member of the entire Ets family to be notably (>2 fold) downregulated in the Mek1/2-ablated brains. However, the Inventors found that seven members of the Ets-family are upregulated in the Inventors' RTK or Ras-driven tumors. By employing a DN-Etv5, the Inventors note that the premature depletion of NSCs and glial hyperproliferation can be blocked downstream of Ras hyperactivity. Nevertheless, it is clear that Nf1 additionally functions in the transitamplifying population. Given that RG and progenitor populations are simultaneously EP-ed, it would follow that DN-Etv5 is sufficient to block the downstream effects of Ras hyperactivity independently in both of these contexts (i.e. rescuing RG and preventing progenitor hyperproliferation). Interestingly, persisting glia resemble the hypertrophic astrocytes and not the OPC-like tumor cells, suggesting that heightened Ets transcriptional activity is necessary for the OPC tumor propagating cell character.

Given the heterogeneity of driver mutations in glioma, it will be interesting to determine whether Ets family transcription factors are a common underlying transcriptional element in glioma or whether other signaling mechanisms are utilized by upstream drivers. Notably, the Inventors have found that there is tumor divergence even with the identical treatment of littermates (FIG. 5D-F). Specifically, Hras EP-ed (or Erbb2 EP-ed) littermates of the same age injected on the same day with the same DNA can yield progenitors falling into disparate glioma subtypes (proneural vs. mesenchymal; FIG. 5F) with different high grade pathological classifications (e.g. anaplastic oligodendroglioma vs. glioblastoma multiforme). Such findings concur with recent findings on tumor diversity in in utero electroporation models and also with data from viral models suggesting that non-GCIMP tumor types evolve from a common proneural subtype. These findings in model systems are reinforced by the emerging findings regarding patient tumor heterogeneity. However, despite the heterogeneity the Inventors saw in small groups of animals, dominant negative inhibition of Ets signaling was able to completely rescue survival in much larger groups of animals, suggesting that reduced Ets signaling may represent a potential blockade for tumor formation. Further, it will be important to determine whether particular Ets family members are necessary for gliomagenesis or if these factors are functionally redundant. Moreover, the Inventors cannot assume that cell type properties are maintained during tumorigenesis as certain cell characteristics can be reacquired during tumorigenesis and subsequent de-differentiation. Specifically, there may be tumor subpopulations that evolve Ets-independent tumor propagating capacities.

The Inventors' results indicate that hyperactivation of the Ras pathway drives depletion of NSCs and the differentiation of progenitors into glial tumor propagating cells. Further, the Inventors have identified Ets family signaling as a necessary downstream factor of Nf1/Ras that mediates tumor propagating cell production. These results may yield insight into previous findings regarding the tumor cell of origin in gliomas being NSCs given the intrinsic hierarchy of stem and progenitor lineages. Rigorous lineage tracing is still necessary to determine if the putative cell(s) of origin represent true differences in tumor subtypes or if these disparities are due to methodological differences that can be reconciled. Nevertheless, these Ets transcription factors and the resulting downstream signaling may present new clinical targets for combating glioma.

Example 31

Additional Study Results

Despite redundancy in DNA recognition across the ETS family, there exists a tissue-specific and target specific role of ETS factors. In fact, analysis of ETS binding sites have shown that the majority of redundant sites are on the proximal promoters of housekeeping genes. The tissue-specific role of ETS factors can largely be attributed to unique protein sequence regions, expression levels, binding partners and post-translational modifications (PTM). In the context of glioma, the transcriptional potency of ETV5 targets may be amplified due to increased activation or stability of ETV5 by PTMs. Alternatively, ETV5 target specificity may be altered in glioma cells as a result of tumor-induced regulatory mechanisms or binding partners. Posttranslational modifications (PTM), including phosphorylation and acetylation profoundly regulate the stability and activation of the PEA3 subfamily. The Pea3 subfamily exhibits a sequence homology of 95%. However, the PTMs regulating ETV5 are understudied and largely extrapolated from what is known of ETV1 or ETV4. It is important to validate PTMs presumed to activate transcriptional activity of ETV5 because unique residues surrounding a PTM site may result in differential effects. For example, mutations flanking the 5'-GGAA-3' core have been shown to affect binding of one Ets factor but not another.

Example 32

Unmodified Etv5 Displays Minimal Transactivation Compared to Activated State

In addition to aforementioned functional investigations of Etv5 in glioma, the Inventors further scrutinize its pathomechanisms in disease progression. Several biochemical studies suggest the necessity for ETV5 activation by PTM beyond upregulation. In preliminary studies, the Inventors assessed whether overexpression of Etv5 in our in vivo model would be sufficient to phenocopy oncogene expression. As mentioned, upon electroporation of driver mutations one observes rapid depletion of radial glia NSC and hyperplasia of electroporated cells. However, electroporation of Etv5 alone failed to elicit these hallmarks, including gliogenesis and increased cell proliferation leading to tumor formation. The lack of a clear phenotype with Etv5 misexpression—along with the previously reference biochemical studies of Etv5—suggests a necessity for posttranslational modification of Etv5 to induce maximal transactivation potential beyond the existence of the increased expression observed in glioma.

To validate the notion that expression levels alone is not sufficient to maximize ETV5 transactivation, the Inventors sought to compare wildtype Etv5 with a synthetic, activated form of the protein—Etv5-VP64. This is a fusion of the ETV5 DBD domain and the VP64 viral transactivation domain. Importantly, this ETV5 fragment lacks most of the known or predicted PTM sites and thus should be constitutively active. To assess transactivation activity, the Inventors transfected a PEA3 responsive luciferase reporter (Pea3-Luc) in the presence of overexpressed Etv5- or Etv5-VP64. Both expression constructs include a tagBFP fluorescence reporter; hence, plasmid molar ratios and luciferase readout were normalized to the tagBFP control vector. Hek293T were employed as they lack of endogenous ETV5 expression and have previously been used for similar luciferase-based studies of glial promoter transactivation. Our data indicate that despite overexpression of Etv5, the Pea3-luc readout is only 1.3-fold higher than cells expressing the tagBFP control vector. On the other hand, the activated Etv5-VP64 increased transcriptional induction by ~2.3-fold (FIG. 16A).

Importantly, these results indicate that, while Etv5 is overexpressed along with other Ets factors in pediatric glioma cells, the characteristic glial phenotype in tumors may be due to specific activation of this cell-fate regulator by PTMs. Specifically, the acidic transactivation domains may exist in a sterically unfavorable conformation in the absence of PTMs, leaving Etv5 in an inactivated state. The acidic transactivation domain has been shown to adopt transient secondary structure to interact with MED25 in transcription initiation.

Example 32

P300 and PKA Synergistically Increase ETV5 Transactivation

Many PTMs identified on ETV1 or ETV4 have been implicated on conserved residues of ETV5. RSK and MSK are MAPK-activated protein kinases required for maximal transcriptional activity of ETV1. Some of these residues are conserved in ETV5 and may elicit the same effects on transcriptional activation. Additionally, ETV1 acetylation at lysine[33] and lysine[116] by the acetyl transferase, P300, increases DNA binding affinity. Interestingly, ETV5 possessed homologous residues for both acetylation sites. The Inventors sought to determine if these affector proteins could incite the same response on ETV5 as they do on ETV1 transactivation. Rsk, Msk or P300 affecters were co-expressed with Etv5 and tested for induction of Pea3-responsive luciferase activity. For all luciferase assays, plasmids encoding tagBFP, Etv5, Etv5-VP64, and affecter proteins (Rsk, Msk and P300) were equimolar during transfection. The Inventors found that P300 best induced transcriptional activity of Etv5 compared to Msk, Rsk and Etv5 alone. However, P300 did not incite Etv5 activation to the level of Etv5-VP64 (FIG. 16B). This is potentially due to incomplete acetylation by P300 on overexpressed Etv5, while each Etv5-VP64 molecule mimics a constitutively active protein.

Previously, a protein kinase A (PKA) consensus phosphorylation site was identified near the N-terminal boundary of the ETS domain in ETV5. Phosphorylation of this site, serine$^{367}$ has been shown to stimulate transcriptional activity on high affinity genomic targets by initiating a conformational change in ETV5. Because this site has been demonstrated to robustly activate ETV5, the Inventors sought to test the effect of PKA overexpression on Pea3 transactivation. The Inventors performed the Pea3-luc reporter assay and found that PKA overexpression in the presence of Etv5 significantly increased Pea3-luc activity compared to tagBFP control. Strikingly, PKA overexpression in the presence of wt Etv5 nearly tripled the luciferase activity of wt Etv5 alone (equimolar transfection of wt Etv5). Also, PKA induced promoter activity similarly to that of Etv5-VP64, which mimics constitutively active Etv5 (FIG. 16C). The robust activity shown by the overexpression of PKA is suggestive of a possible mechanism activating ETV5 in tumor cells.

Most PTMs implicated for ETV5 have not been scrutinized for effect on ETV5-specific transactivation. Moreover, the tissue- and disease-specific mechanisms of ETV5 modifications remain undescribed. Most previous studies are limited to in vitro, cell-free biochemistry analyses. While the Inventors have evidence that P300 and PKA modifications of ETV5 robustly activate Etv5, it is likely that multiple PTMs may co-exist in a complex and multifaceted network of regulation. Since P300 acetylation of lysine residues are not theoretically mutually exclusive with PKA phosphorylation of serine, the Inventors sought to determine if these PTMs may activate Etv5 synergistically. The Inventors tested combinations of Rsk, P300 and PKA in the presence of wt Etv5 to determine transactivation by Pea3-luc activity. Remarkably, a combination of P300 and PKA resulted in luciferase activity greater than two-fold that of constitutively active Etv5-VP64 (FIG. 16D). These findings demonstrate the necessity for PTMs for activation of Etv5 to reach high levels of transactivation and allude to a complex network of transcription factor regulation beyond expression levels.

TABLE 1

Plasmids created for this study

| | Donor plasmid(s) | Recipient plasmid |
|---|---|---|
| General membrane fluorescent reporter gene | | |
| Ufek PB | Ufek | pZGs |
| pCag Clover-F PB | Clover cDNA | pCagen EGFP PB |
| Ufok PB | Ufok (mOrange2 cDNA) | Ufek PB |
| pCag TD-tomato PB | Td-tomato cDNA) | pCagen EGFP PB |
| pBase derivatives | | |
| pCag hypBase | Gene synthesis | pCagen EGFP PB |
| pCag hypBase-HA | Gene synthesis | pCagen EGFP PB |
| Nuclear reporter genes | | |
| pCag TagBFP2-V5-nls PB | Site-directed mutagenesis of TagBFP | pCagen PB |
| pCag TagBFP2-3XFlag-nls PB | TagBFP2-V5 | pCag TagBFP2-V5-nls PB |
| pCag TagBFP2-HA-nls PB | TagBFP2-V5 | pCag TagBFP2-V5-nls PB |
| pEF1 Bgla-HA PB | gene synthesis of 3XHA-nls-beta-glucosidase | pEF1 Bos Rbpj |
| Erbb2 expression vectors | | |
| pUb v5 Erbb2 V664E PB | pSV-Erbb2 V664E | Ufek PBL |
| pUb v5 Erbb2 WT PB | pSV-Erbb2 WT | Ufek PBL |
| pUb Clover T2a v5 Erbb2 V664E PB | pUb v5 Erbb2 V664E PB | pUb v5 Erbb2 V664E PB |
| Hras Expression vectors | | |
| pUB EGFP-Hras WT PB | Site-directed mutagenesis of pUB EGFP-Hras G12 VPB | pUB EGFP-Hras G12V PB |
| pUB EGFP-Hras G12v PB | Addgene mEGFP-Hras G12V; Addgene plasmid 18666 | Ufek PBL |
| pUB mRuby2-Hras G12V PB | mRuby2 cDNA | pUB EGFP-Hras G12V PB |

TABLE 1-continued

| | Plasmids created for this study | |
|---|---|---|
| | Donor plasmid(s) | Recipient plasmid |
| Kras Expression vectors | | |
| pUB EGFP-Kras G12V PB | cDNA amplification and mutatgenesis from mouse brain | pUB EGFP-Hras G12v PB |
| Pdgfra Expression vectors | | |
| pUB Pdgfra D842V PBL | BC053036 clone from Open Biosystems followed by site-directed mutatgenesis | Ufek PBL |
| Cre dependent expression vectors | | |
| pCag loxP Stop loxP EGFP-Hras G12V PB | pCag loxP Stop LoxP EGFP; pUB EGFP-Hras G12V PB | pCagen PB |
| pCag loxP Stop loxP EGFP-F PB | pCag loxP Stop LoxP EGFP | pCagen PB |
| pCag FLEx EGFP WPRE PB | PCR-addition of mutant LoxP pairs to EGFP | pCagen WPRE PB |
| shRNA Expression vectors | | |
| pCag miR30 PB | pCag mir30; Addgene plasmid 14758 | pCagen PB |
| pCag miR-E PB | PCR-addition of variant sequences from mir30 and XhoI/EcoRi PCR Shagging of templates | pCag miR PB |
| SENSOR shRNA test plasmids | | |
| pUfek SENSOR PB | Ultramer-amplification using primer site engineered 3'UTR of EGFP in Ufek PB | pUfek PB |
| Variants | | |
| pUfek PBL Nf1-618 SENSOR | | |
| pUfek PBL Nf1-789 SENSOR | | |
| pUfek PBL Nf1-3244 SENSOR | | |
| pUfek PBL Nf1-6072 SENSOR | | |
| pUfek PBL Nf1-6992 SENSOR | | |
| Etv5 related plasmids | | |
| pCag-TagBFP2-V5-3XFlag-nls-P2A-EGFP-Hras G12V PB | | pCag-TagBFP2-V5-Etv5DBD-nls-P2A-EGFP-Hras G12V PB (i.e. DN-Etv5) |
| pCag-TagBFP2-V5-Etv5DBD-nls-P2A-EGFP-Hras G12V PB (i.e. DN-Etv5) | | pCag-TagBFP2-V5-Etv5DBD PB |
| pCag-TagBFP2-V5-Etv5DBD PB | amplification from cDNA | pCag-TagBFP2-V5 PB |
| pCag-TagBFP2-V5-Etv5-VP64PB | VP64 gene synthesis | pCag-TagBFP2-V5-Etv5DBD PB |
| pCag-TagBFP2-V5-Etv5-full length PB | amplification from cDNA | pCag-TagBFP2-V5 PB |
| Genetic MRI tracer | | |
| pUB Ferritin-H + L Flag PB | Ferritin cDNA | Ufek PBL |
| Additional plasmids employed in this study | | |

TABLE 1-continued

Plasmids created for this study

| Donor plasmid(s) | Recipient plasmid |
|---|---|

| General membrane fluorescent reporter gene | Source |
|---|---|
| pCag pBase | |
| pCag TagBFP-V5-nls | |
| pZGs | |
| Glast-Cre | |
| pCMV-EGFP-NF1 | |

TABLE 2

Antibodies used in this study

| Antibody | Abbreviation | Species | Vendor | Catalogue Number | Dilution used |
|---|---|---|---|---|---|
| acyl-CoA synthetase bubblegum family member 1 | Acsbg1 | rb | Abcam | Ab65154 | 1:2500 |
| achaete-scute homolog 1 | Ascl1 | rb | Cosmo Bio USA | SAC-SK-T01-003 | 1:1000 |
| Actin | | ms | Millipore | MAB1501 | 1:1000 |
| Acetylated Tubulin | Ac-tub | ms | Sigma-Aldrich | T6793 | 1:1000 |
| aldehyde dehydrogenase fam 1, memb 1 | ALDH1L1 | rb | EnCor Biotechnology Inc. | RPCA-ALDH1L1 | 1:2000 |
| Aldolase C | Aldoc | gt | Santa Cruz Biotechnology | sc-12065 | 1:100 |
| Doublecortin | Dcx | gt | Santa Cruz Biotechnology | sc-8066 | 1:250 |
| DsRed | | rb | Clontech | 632496 | 1:1000 |
| DsRed | | rt | Chromotech | 5f8 | 1:1000 |
| Green Fluorescent Protein | GFP | ck | Abcam | ab13970 | 1:5000 |
| Green Fluorescent Protein | GFP | gt | Abcam | ab5450 | 1:1000 |
| Green Fluorescent Protein | GFP | rb | Invitrogen | G10362 | 1:1000 |
| Erbb2 | | rb | Cell Signaling | 2165 | 1:250 |
| Er81 (Etv1) | | rb | Abcam | ab81086 | 1:500 |
| Flag Epitope | FLAG | ms | Sigma-Aldrich | F1804 | 1:1000 |
| Flag Epitope | FLAG | rb | Sigma-Aldrich | F7425 | 1:1000 |
| Glial Fibrillary Acidic Protein | GFAP | gp | Synaptic Systems | 173004 | 1:1000 |
| Glial Fibrillary Acidic Protein | GFAP | rb | Dako | Z 0334 | 1:500 |
| Glutamine Synthetase | GS | rb | Sigma-Aldrich | G 2781 | 1:10,0000 |
| Hemagglutinin Epitope | HA | ms | Covance | MMS-101R | 1:1000 |
| Hemagglutinin Epitope | HA | rb | Cell Signaling | 3724 | 1:1000 |
| Hemagglutinin Epitope | HA | rt | Roche | 3F10 | 1:1000 |
| Ki67 | Ki67 | rb | Vector Labs | VP-RM04 | 1:500 |
| beta Galactosidase | LacZ | ck | Abcam | ab9361 | 1:5000 |
| Neurofibromin | Nf1 | rb | Santa Cruz Biotechnology | sc-67 | 1:500 |
| NFIA | | rb | Abcam | ab11988 | 1:1000 |
| NG2 | | rb | Millipore | AB5320 | 1:250 |
| Olig2 | | gt | R&D Systems | AF2418 | 1:250 |
| Olig2 | | rb | Millipore | AB9610 | 1:1000 |
| phosphor-Akt | pAkt | rb | Cell Signaling | 4060 | 1:250 |
| phosphor-p44/42 MAPK (Erk1/2) | pErk | rb | Cell Signaling | 4370 | 1:500 |
| CD140a | PGDFR-a | rt | BD Pharminogen | 558774 | 1:250 |
| S-100 Calcium-Binding Protein, Beta | S100B | rb | Sigma-Aldrich | S2532 | 1:500 |

TABLE 2-continued

Antibodies used in this study

| Antibody | Abbreviation | Species | Vendor | Catalogue Number | Dilution used |
|---|---|---|---|---|---|
| SRY-box containing gene 10 | Sox10 | gt | R&D Systems | AF2864 | 1:200 |
| SRY (sex determining region Y)-box 2 | Sox2 | gt | Santa Cruz Biotechnology | sc-17320 | 1:500 |
| V5 Epitope | V5 | gt | Abcam | Ab95038 | 1:1000 |
| V5-Epitope | V5 | ms | Invitrogen | R960-25 | 1:10,0000 |
| Vimentin | | ck | Millipore | AB5733 | 1:2000 |

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art. Among these variations, without limitation, are the compositions for, and methods of, treating glioma by targeting of Nf1-Ras-Ets pathway, compositions capable of modulating glioma initiation and maintenance and/or modulating Nf1-Ras-Ets, and other methods that relate to the teachings of the invention, techniques and composition and use of solutions used therein, and the particular use of the products created through the teachings of the invention. Various embodiments of the invention can specifically include or exclude any of these variations or elements.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventor for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law.

Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

The invention claimed is:

1. A method of treating glioma in a subject in need thereof comprising:
   providing a quantity of a composition which blocks glioma initiation and/or maintenance; and
   administering the quantity of the composition to the subject in need thereof, wherein blocking of glioma initiation and/or maintenance treats glioma in the subject, and wherein the composition is a dominant negative ETV5.

2. The method of claim 1, wherein the composition which blocks glioma initiation and/or maintenance modulates Ets.

3. The method of claim 2, wherein modulating Ets comprises an alteration in Ets binding to a target.

4. The method of claim 2, wherein modulating Ets comprises an alteration in Ets expression level.

5. The method of claim 3, wherein the alteration in Ets binding to a target suppresses transcriptional activity.

* * * * *

```
                        SEQUENCE LISTING

<160> NUMBER OF SEQ ID NOS: 2

<210> SEQ ID NO 1
<211> LENGTH: 22
<212> TYPE: DNA
<213> ORGANISM: Mus musculus

<400> SEQUENCE: 1
tccggatgaa tttacaaagc ta                                           22

<210> SEQ ID NO 2
<211> LENGTH: 21
<212> TYPE: DNA
<213> ORGANISM: Homo sapiens

<400> SEQUENCE: 2
ccccacgagt tcaccaagct g                                            21
```